United States Patent
Tector

(10) Patent No.: US 11,666,039 B2
(45) Date of Patent: *Jun. 6, 2023

(54) DOUBLE KNOCKOUT (GT/CMAH-KO) PIGS, ORGANS AND TISSUES

(71) Applicant: Indiana University Research and Technology Corporation, Indianapolis, IN (US)

(72) Inventor: A. Joseph Tector, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 261 days.

This patent is subject to a terminal disclaimer.

(21) Appl. No.: 16/855,905

(22) Filed: Apr. 22, 2020

(65) Prior Publication Data

US 2021/0076647 A1  Mar. 18, 2021

Related U.S. Application Data

(60) Continuation of application No. 15/848,870, filed on Dec. 20, 2017, now Pat. No. 10,667,500, which is a division of application No. 14/436,963, filed as application No. PCT/US2013/066387 on Oct. 23, 2013, now Pat. No. 9,888,674, which is a continuation of application No. 13/804,365, filed on Mar. 14, 2013, now abandoned.

(60) Provisional application No. 61/717,845, filed on Oct. 24, 2012.

(51) Int. Cl.

| | | |
|---|---|---|
| *A01K 67/027* | (2006.01) | |
| *C12N 15/877* | (2010.01) | |
| *C12N 9/10* | (2006.01) | |
| *C12N 9/22* | (2006.01) | |
| *C12N 9/40* | (2006.01) | |
| *C12N 9/02* | (2006.01) | |
| *A61K 35/407* | (2015.01) | |
| *C12N 15/85* | (2006.01) | |
| *C12N 15/90* | (2006.01) | |

(52) U.S. Cl.
CPC ........ *A01K 67/0276* (2013.01); *A61K 35/407* (2013.01); *C12N 9/0071* (2013.01); *C12N 9/1048* (2013.01); *C12N 9/22* (2013.01); *C12N 9/2465* (2013.01); *C12N 15/8509* (2013.01); *C12N 15/8778* (2013.01); *C12N 15/907* (2013.01); *A01K 2217/00* (2013.01); *A01K 2217/075* (2013.01); *A01K 2217/15* (2013.01); *A01K 2227/108* (2013.01); *A01K 2267/025* (2013.01); *C07K 2319/80* (2013.01)

(58) Field of Classification Search
None
See application file for complete search history.

(56) References Cited

U.S. PATENT DOCUMENTS

| | | |
|---|---|---|
| 5,352,240 A | 10/1994 | Ross |
| 5,560,911 A | 10/1996 | Koren |
| 5,705,732 A | 1/1998 | Sims |
| 5,728,554 A | 3/1998 | Bayer |
| 5,728,812 A | 3/1998 | Koren |
| 5,821,117 A | 10/1998 | Sandrin |
| 5,846,715 A | 12/1998 | Purcell |
| 5,849,991 A | 12/1998 | d'Apice |
| 5,891,698 A | 4/1999 | Prieto |
| 5,922,577 A | 7/1999 | Defrees |
| 6,140,116 A | 10/2000 | Dinsmore |
| 6,147,276 A | 11/2000 | Campbell |
| 6,166,288 A | 12/2000 | Diamond |
| 6,204,431 B1 | 3/2001 | Prieto |
| 6,245,890 B1 | 6/2001 | Zhu |
| 6,258,353 B1 | 7/2001 | Isacson |
| 6,258,998 B1 | 7/2001 | Damiani |
| 6,331,418 B1 | 12/2001 | Roth |
| 6,331,658 B1 | 12/2001 | Cooper |
| 6,399,758 B1 | 6/2002 | Sandrin |
| 6,423,316 B1 | 7/2002 | Riesbeck |
| 6,444,205 B2 | 9/2002 | Dinsmore |
| 6,548,741 B2 | 4/2003 | DeSousa |
| 6,566,102 B1 | 5/2003 | Switzer |
| 6,610,501 B2 | 8/2003 | Zhu |
| 6,849,448 B1 | 2/2005 | D'Apice |
| 7,001,998 B2 | 2/2006 | McKenzie |
| 7,038,107 B2 | 5/2006 | Cui |
| 7,166,278 B2 | 1/2007 | Zhu |
| 7,368,284 B2 | 5/2008 | Koike |

(Continued)

FOREIGN PATENT DOCUMENTS

| | | |
|---|---|---|
| CA | 2364279 | 9/2000 |
| WO | 02/88351 | 11/2002 |

(Continued)

OTHER PUBLICATIONS

Wood, et al. (Jun. 2011) "Targeted Genome Editing Across Species Using ZFNs and TALENs", Science, 333: 307. (Year: 2011).*

Jinek, et al. (2012) "A programmable Dual-RNA-Guided DNA Endonuclease in Adaptive Bacterial Immunity", Science, 337(6096): 816-21. (Year: 2012).*

Estrada, et al., Evaluation of human and non-human primate antibody binding to pig cells lacking GTIA1/CMAH/B4GalNT2 genes, Xenotransplantation, 2015, 22:194-202.

Ekser, et al., Pig Liver Xenotransplantation as a Bridge to Allotransplantation: Which Patients Might Benefit?, Transplantation, 2009, vol. 88, No. 9; 9 pages.

(Continued)

*Primary Examiner* — Robert M Kelly

(74) *Attorney, Agent, or Firm* — Faegre Drinker Biddle & Reath LLP

(57) ABSTRACT

The invention provides double knockout transgenic pigs (GT/CMAH-KO pigs) lacking expression of any functional αGAL and CMAH. Double knockout GT/CMAH-KO transgenic organs, tissues and cells are also provided. Methods of making and using the GT/CMAH-KO pigs and tissue are also provided.

21 Claims, 16 Drawing Sheets

Specification includes a Sequence Listing.

(56) References Cited

U.S. PATENT DOCUMENTS

| | | | |
|---|---|---|---|
| 7,432,344 | B1 | 10/2008 | Lechler |
| 7,485,769 | B2 | 2/2009 | Murakami |
| 7,531,715 | B1 | 5/2009 | Campbell |
| 7,547,522 | B2 | 6/2009 | Hawley |
| 7,547,816 | B2 | 6/2009 | Day |
| 7,560,538 | B2 | 7/2009 | Koike |
| 7,582,741 | B2 | 9/2009 | Jones |
| 7,626,075 | B2 | 12/2009 | Beschorner |
| 7,682,794 | B2 | 3/2010 | Varki |
| 7,732,180 | B2 | 6/2010 | Koike |
| 7,741,539 | B2 | 6/2010 | Gorr |
| 7,795,493 | B2 | 9/2010 | Phelps |
| 8,034,330 | B2 | 10/2011 | Zhu |
| 8,084,219 | B2 | 12/2011 | Varki |
| 8,088,969 | B2 | 1/2012 | Elliott |
| 8,097,598 | B2 | 1/2012 | Lechler |
| 8,106,251 | B2 | 1/2012 | Ayares |
| 8,232,448 | B2 | 7/2012 | Varki |
| 8,324,449 | B2 | 12/2012 | McQuillan |
| 8,541,231 | B2 | 9/2013 | Varki |
| 8,709,400 | B2 | 4/2014 | Hammerman |
| 8,716,240 | B2 | 5/2014 | DeFrees |
| 8,846,373 | B2 | 9/2014 | Geisler |
| 8,907,163 | B2 | 12/2014 | Bakker |
| 8,980,583 | B2 | 3/2015 | Lin |
| 9,888,674 | B2 | 2/2018 | Tector |
| 10,667,500 | B2 * | 6/2020 | Tector ................ C12N 9/0071 |
| 2002/0031494 | A1 | 3/2002 | Sandrin |
| 2002/0081654 | A1 | 6/2002 | Sandrin |
| 2002/0152488 | A1 | 10/2002 | Cooper |
| 2003/0024002 | A1 | 1/2003 | Colman |
| 2003/0131365 | A1 | 7/2003 | Cooper |
| 2003/0162163 | A1 | 8/2003 | Burgess |
| 2003/0165480 | A1 | 9/2003 | Zhu |
| 2004/0133932 | A1 | 7/2004 | Cooper |
| 2004/0268424 | A1 | 12/2004 | Phelps |
| 2006/0242722 | A1 | 10/2006 | Hawley |
| 2006/0294610 | A1 | 12/2006 | Koike |
| 2008/0250517 | A1 | 10/2008 | Colman |
| 2009/0043383 | A1 | 2/2009 | McGregor |
| 2009/0049563 | A1 | 2/2009 | Harris |
| 2010/0293624 | A1 | 11/2010 | Varki |
| 2010/0333218 | A1 | 12/2010 | Cooper |
| 2011/0038841 | A1 | 2/2011 | Ayares |
| 2011/0195921 | A1 | 8/2011 | Varki |
| 2011/0301341 | A1 | 12/2011 | Zhu |
| 2012/0045816 | A1 | 2/2012 | Ghaderi |
| 2012/0060230 | A1 | 3/2012 | Collingwood |
| 2012/0255047 | A1 | 10/2012 | Phelps |
| 2013/0111614 | A1 | 5/2013 | McGregor |
| 2014/0115728 | A1 | 4/2014 | Tector |
| 2014/0178365 | A1 | 6/2014 | Ghaderi |
| 2015/0018966 | A1 | 1/2015 | Bolland |
| 2018/0153146 | A1 | 6/2018 | Tector |

FOREIGN PATENT DOCUMENTS

| | | |
|---|---|---|
| WO | 2004/028243 | 4/2004 |
| WO | 2007/035213 | 3/2007 |
| WO | 2010/008562 | 1/2010 |
| WO | 2010/008564 | 1/2010 |
| WO | 2011/017315 | 2/2011 |
| WO | 2013/169929 | 11/2013 |
| WO | 2016/065046 | 4/2016 |

OTHER PUBLICATIONS

Dr. Demburg (2008) lecture slides at http://mcb.berkeley.edu/courses/mcb142/lecture%20topics/Demburg/Lecture6_ChapterB screenviewing.pdf, no journal, no volume, Published online by University of California Berkley, Berkley, California, 25 pages.

Diaz, et al., Flow Cytometry Complement-Mediated Cytotoxicity Assay Detects Baboon Xenoantibodies Directed to Porcine Epitopes Undetected by Hemolytic Assay, Transplant Immunology, 2004, 13(4): 313-317.

Della-Guardia, et al., Antibody-Mediated Rejection: Hyperacute Rejection Reality in Liver Transplantation? A Case Report, Transplantation Proceedings, 2008, 40:870-871.

David K.C. Cooper Declaration under 37 C.F.R. 1.132, Jul. 27, 2010; 12 pages.

D'Apice, et al., Gene-Modified Pigs, Xenotransplantation, 2008, 15:87-90.

D'Apice et al., Xenotransplantation: The Next Generation of Engineered Animals, Transpl Immunol, Jun. 2009, 21(2):111-115; 9 pages.

Cowan and Rieben, "Modifying the Glycome in Pigs for Xenotransplantation", Transplantation, Mar. 2016, vol. 100, Issue 3, p. 485-486.

Cooper et al., Progress in Pig-to-Nonhuman Primate Transplantation Models (1998-2013): A Comprehensive Review of the Literature, Xenotransplantation, Sep. 2014, 21(5), 397-419; 35 pages.

Conchon, et al., Generation of CMAH-/-piglets on GAL-I-genertic Background, Oral Communication 8:Tg Pigs and Animal Models, Nov. 13, 2013 (Abstract Only).

Christensen, et al., Humans Lack iGb3 Due to the Absence of Functional iGb3-Synthase: Implications for NKT Cell Development and Transplantation, PLoS Biology, 2008, 6(7):e172, pp. 1527-1538.

Chihara, et al., Primary Porcine Kupffer Cell Phagocytosis of Human Platelets Involves the CD18 Receptor, Transplantation, 2011, 92(7):739-744.

Chen, et al., Cryptic Natural Autoantibodies and Co-Potentiators, Autoimmunity Reviews, 2008, 7(6):431-434.

Chen et al., The Role and Anti-non-Gal Antibodies in the Development of Acute Humoral Xenograft Rejection of hDAF Transgenic Porcine Kidneys in Baboons Receiving Anti-Gal Antibody Neutralization Therapy, Transplantation, 2006, 81(2):273-283.

Chen, et al., Acute Rejection is Associated with Antibodies to non-Gal Antigens in Baboons Using Gal-kncokout Pig Kidneys, Nat. Med. 2005, 11(12):1295-1298.

Chatzipetrou et al., Thrombocylopenia After Liver Transplantation, Transplantation, 1999, 67(5):702-706 (Abstract Only).

Chatzipetrou et al., Thrombocytopenia After Liver Transplant, Transplant, 31/15/1999, p. 702-706, v. 67-5.

Chari et al., "Treatment of Jepatic Failure with Ex Vivo Pig-Liver Perfusion Followed by Liver Transplantation", New England Journal of Medicine, Jul. 28, 1994, vol. 331, pp. 234-237.

Chandrasekharan, et al., Proprietary Science, Open Science and the Role of Patent Disclosure: The Case of Zine-Finger Proteins, Nature Biotechnology, 2009, 27(2):140-144.

Byrne, et al., Proteomic Identification of Non-Gal Antibody Targets After Pig-to-Primate Cardiac Xenotransplantation, Xenotranplantation, 2008, 15(4):268-276.

Butler, et al., Recent advances in genome editing and creation of genetically modified pigs, International Journal of Surgery, 2015, 23(8):217-222.

Busse, "Transplant Rejection", Medicine Plus, http://www.nlm.nih.gov/medlineplus/ency/article/000815.htm, Jun. 26, 2013.

Burlak, et al., The Fate of Human Platelets Perfused Through the Pig Liver: Implications for Xenotransplantation, Xenotransplantation, 2010, 17:350-361.

Burlak, et al., Identification of Human Preformed Antibody Targets in GTKO Pigs, Xenotransplantation, 2012, 19:92-101.

Breimer, Gal/non-Gal Antigens in Pig Tissues and Human non-Gal Antibodies in the GalT-KO Era, Xenotransplantation, 2011, 18:215-228.

Branski, et al., A Porcine Model of Full-Thickness Burn, Excision and Skin Autografting Burns, 2008, 34(8):1119-1127.

Bhaskar, et al. (2011) "Autogenous skull flaps stored frozen for more than 6 months: do they remain viable?" Journal of Clinical Neuroscience: The Official Journal of the Neurological Society of Australasia, 18(12)1960-03 (Abstract Only).

Becker, et al., Temporary Wound Dressing of Burns and Fresh, Sterile, Frozen Porcine Skin, Annals of Burns and Fire Disasters, 1998,11(3):171-175.

(56) References Cited

OTHER PUBLICATIONS

Baumann, et al., Reactivity of Human Natural Antibodies to Endothelial Cells from Gal[alpha](1,3) Gal-Deficient Pigs, Transplantation, 2007, 83(2):193-201.

Basnet, et al., Deficiency of N-glycolylneuraminic Acid and Gal(alpha)1-3GalBI-4GlcNAc Epitopes in Xenogeneic Cells Attenuates Cytotoxicity of Human Natural Antibodies, Xenotransplantation, 2010, 17:440-448.

Artificial Liver Could be Powered by Swine Cells, Medical News Today, Mar. 2, 2013, http://www.medicalnewstoday.com/releases/257027.php; 4 pages.

Addgene, Plasmid 42230: pX330-U6-Chimeric_BB-CHB_hSpCas9 Plasmid Data, http://www.addgene.orge/42230, printed Sep. 26, 2013; 2 pages.

Ziak, et al., Megalin in Normal Tissues and Carcinoma Cells Carries oligo/poly a2,8 Deaminoneuraminic Acid as a Unique Post-translational Modification, Glycoconjugate Journal, 1999, 16:185-188.

Ziak, et al., Identification of Megalin as the Sole Rat Kidney Sialoglycoprotein Containing Poly a2,8 Deaminoneuraminic Acid, J. Am. Soc. Nephrol, 1999, 10:203-209.

Zeyland, et al., "The Current State of Xenotransplantation", Journal of Applied Genetics, May 1, 2015, vol. 56, pp. 211-218.

Wang, et al., Erythrocytes from GGTA1/CMAH Knockout Pigs: Implications for Xenotransfusion and Testing in Non-Human Primates, Xenotransplantation, 2014, 21(4):376-384 (Abstract Only).

Waghmare, et al., Gene Targeting and Cloning in Pigs Using Fetal Liver Derived Cells, Journal of Surgical Research, 2011, 171:e223-e229.

Troy, et al., The Use of EZ Derm(R) in Partial-Thickness Burns: An Institutional Review of 157 Patients Journal ID: ePlasty, Publisher, Open Science Company LLC, vol. 13, E-location ID: e14, Published Mar. 7, 2013, pp. 108-119.

Tahara, et al., Immunological Property of Antibodies Against N-Glycolylneuraminic Acid Epitopes in Cylidine Monophospho-N-Acetylneuraminic Acid Hydroxylase-Deficient Mice, Journal of Immunology, 2010, 184:3269-3275.

Shimizu, et al., Thrombotic Microangiopathy Associated with Humoral Rejection of Cardiac Xenografts from a1,3 Galactosyltransferase Gene-Knockout Pigs in Baboons, American Journal of Pathology, 2008, 172 (6): 1471-1481.

Shimizu, et al., Pathologic Characteristics of Transplanted Kidney Xenografts, J. Am. Soc. Nephrol., 2012, 23:225-235.

Servetiaz, et al., Natural Anti-Endothelial Cell Antibodies, Autoimmunity Reviews, 2008, 7(6):426-430.

Seong, et al., Hydrophobicity: An Ancient Damage-Associated Molecular Pattern that Initiates Innate Immune Responses, Nature Reviews Immunology, 2004, 4:469-478.

Scobie, et al., Long-Term IgG Response to Porcine Neu5Gc Antigens without Transmission of PERV in Burn Patients Treated with Porcine Skin Xenografts, Journal of Immunology, 2013, 191:2907-2915.

Sandrin, et al., Genetic Engineering for Xenotransplantation, Journal of Cardiac Surgery, 2001, 16(6):448-457 (Abstract Only).

Sandrin et al, Gala(1,3) Gal, the Major Xenoantigen(s) Recognised in Pigs by Human Natural Antibodies, Immunological Reviews, 1994, 141:169-190.

Saethre, et al., Characterization of Natural Human Anti-Non-Gal Antibodies and Their Effect on Activation of Porcine Gal-Deficient Endothelial Cells, Transplantation, 2007, 84(2):244-250.

International Search Report and Written Opinion issued by the European Patent Office, dated Jan. 14, 2014, for International Patent Application No. PCT/US2013/066387; 13 pages.

Park, et al., Alpha 1,3-Galactosyltransferase Deficiency in Pigs Increases Sialytransferase Activities that Potentially Raise Non-Gal Xenoantigenicity, Journal of Biomedicine and Biotechnology, vol. 2011, Article ID 560850; 8 pages.

Paris, et al., ASGR1 Expressed by Porcine Enriched Liver Sinusoidal Endothelial Cells Mediates Human Platelet Phagocytosis in Vitro, Xenotransplantation, 2011, 18:245-251.

Pankov, et al., Fibronectin at a Glance, Journal of Cell Science, 2002, 115:3861-3863.

Padler-Karavani, et al., Diversity in Specificity, Abundance, and Composition of Anti-Neu5Gc Antibodies in Normal Humans: Potential Implications for Disease, Glycobiology, 2008, 18(10):818-830.

Orlando, et al., Megalin (gp330) Possesses an Antigenic Epitope Capable of Inducing Passive Heymann Nephritis Independent of the Nephritogenic Epitope in Receptor-Associated Protein, Journal of the American Society of Nephrology, 1995, 6:61-67.

No Author, Recent Patents in Xenotransplantation, Nature Biotechnology, vol. 35 No. 12 Dec. 2017, p. 1142.

Mosher, Physiology of Fibronectin, Annual Review of Medicine, 1984, 35:561-575.

McFadden Researches Using Pig Tissue to Help Heal Human Wounds, http://www.wndu.com/mmm/head-lines/59279087.html, copyright 2002-2013, Gray Television Inc., printed Sep. 11, 2013; 4 pages.

McCaughan et al., "Thrombocytopenia post-Liver Transplantation. Correlations with Pre-operative platelet count, blood transfusion requirements, allograft functions and outcome," J. Hepatol, Sep. 1992, p. 16-22, v16 (1-2).

Matou-Kovd, et al., Heading Effect Recombined Human/Pig skin on Dermal Defects, Ann. Medit. Burns Club, 1994, vol. 7, N. 3; 5 pages.

Lutz, et al., Naturally Occurring Auto-Antibodies in Homeostasis and Disease, Trends in Immunology, 2008, 30(1):43-51.

Lutz, et al., Double Knockout Pigs Deficient in N-glycolylneuraminic Acid and Galactose a-1,3 Galactose Reduce the Humoral Barrier to Xenotransplantation, Xenotransplantation, 2013, 20:27-35.

Liver-Humoral Rejection, http://tpis1.upmc:81/tpis/liver/lrejhum/html, printed Oct. 22, 2012, 6 pages.

Li et al., Isolation, Characterization, and Nuclear Reprogramming of Cell Lines Derived from Porcine Adult Liver and Fat, Cellular Reprogramming, 2010, 12(5):599-607.

Li et al., Biallelic Knockout of the a-1, 3 Galactosyltransferase Gene in Porcine Liver-Derived Cells Using Zinc Finger Nucleases, Journal of Surgical Research, 2013, 181(1):e39-e45.

Li et al., Biallelic Knockout of the a-1,3 Galactosyltransferase Gene in Porcine Liver-Derived Cells Using Zinc Finger Nucleases, Journal of Surgical Research, 2012, xxx:E1-E7.

Li Ping et al., "Biallelic knockout of the alpha-1, 3 glactosyltransferase gene in porcine liver-derived cells using zinc finger nucleases", Journal of Surgical Research, vol. 181, No. 1, Jul. 3, 2012; pp. E39-E45.

Le Bas-Bernardet, et al., Xenotransplantation of Galactosyl-Transferase Knockout, CD55, CD59, CD39, and Fucosyl-Transferase Transgenic Pig Kidneys into Baboons, Transplantation Proceedings, 2011, 43:3426-3430.

Laurencin, et al., Xenotransplantation in Orthopaedic Surgery, Journal of the American Academy of Orthopaedic Surgeons, 2008, 16:4-8.

International Preliminary Report on Patentability issued by The International Bureau of WIPO, dated May 7, 2015, for International Patent Application No. PCT/US2013/066387; 7 pages.

Ikeda, et al., A Cloning of Cytidine Monophospho-N-Acetylneuraminic Acid Hydroxylase From Porcine Endothelial Cells, Transplantation Proceedings 2012, 44:1136-1138.

Human Body Disease, Skin Grafts and Artificial Skin, http://humanbodydisease.com/skin-grafts-196.html, Posted on Mar. 8, 2009; 5 pages.

Hoyle, United Therapeutics Would Harvest Pig Lungs for Human Use, Triangle Business Journal, Aug. 10, 2012, 2012 WLNR 17004975; 3 pages.

Hisashi et al, Rejection of Cardiac Xenografts Transplanted from a 1,3-Galactosyltransferase Gene-Knockout (GalT-KO) Pigs to Baboons, Am. J. Transplant, 2008, 8(12):2516-2526.

Hauschild, et al., Efficient Generation of a Biallelic Knockout in Pigs Using Zine-Finger Nucleases, PNAS, 2011, 108(29):12013-12017.

Hara, at al, "Human Dominant-Negative Class II Transactivator Transgenic Pigs-Effect on the Human Anti-Pig T-Cell Immune Response and Immune Status," Immunology, Sep. 1, 2013, vol. 140; pp. 36-46.

(56) References Cited

OTHER PUBLICATIONS

Griesemer, et al., Results of Gal-Knockout Porcine Thymokidney Xenografts, Am. J. Transplant, 2009, 9(12):2669-2678.
Grewal, et al., The Ashwell Receptor Mitigates the Lethal Coagulopathy of Sepsis, Nat. Med., 2008, 14(6):648-655.
Google Search Result, no author, no journal, no volume, no title, Aug. 8, 2016; 2 pages.
Ghaderi, et al., Implications of the Presence of N-glycolylneuraminic Acid in Recombinant Therapeutic Glycoproteins, Nat. Biotechnol., 2010, 28(8):863-867.
George, et al., Defects in Mesoderm, Neural Tube and Vascular Development in Mouse Embryos Lacking Fibronectin, Development, 1993, 119:1079-1091.
Galli, et al., Genetic Engineering Including Superseding Microinjection: New Ways to Make GM Pigs, Xenotransplantation, 2010, 17(6):397-410.
Farquhar, et al., The Heymann Nephritis Antigenic Complex: Megalin (gp330) and RAP, Journal of the American Society of Nephrology, 1995, 6:35-47.
Evered, et al., The Footprint of Antibody Bound to Pig Cells: Evidence of Complex Surface Topology, Biochemical and Biophysical Research Communication, 2003, 301(3):751-757.

\* cited by examiner

```
         WT:AAACTCCTGAACTACAA- - - -GGCTCGGCTGGTGAAGGA      SEQ ID NO: 16
CMAH P2-P5:AAACTCCTGAACTACAAGGAAGGCTCGGCTGGTGAAGGA          SEQ ID NO: 17

WT:GTCATCTTTTACATCATGGTGGATGATATCTCCAGGATGCC      SEQ ID NO: 18
GGTA1 P2-P5:GTCATCTTTTACATCATG- - -AATGATATCTCCAGGATGCC    SEQ ID NO: 19
```

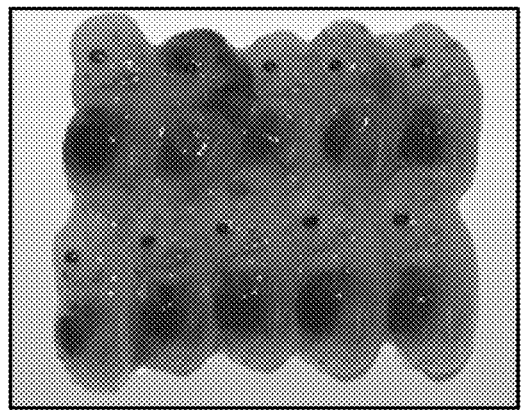

FIG. 9A

| | | | |
|---|---|---|---|
| GGTA1 | CTTTTCCCAGGAGAAAATAATGAATGTCAAAGGAAGAGTGGTTCT | WT | SEQ ID NO: 24 |
| Fetus1 | CTTTTCCCAGGAGAAAATAATGAATGT-AAAGGAAGAGTGGTTCT | -1bp | |
| | CTTTTCCCAGGAGAAAATAATGAATGTCAAAGGAAGAGTGGTTCT (T) | +1bp | |
| Fetus2 | CTTTTCCCAGGAGAAAATAAT------CAAAGGAAGAGTGGTTCT | -6bp | |
| | CTTTTCCCAGGAGAAAATAATGAATGTCAAAGGAAGAGTGGTTCT (AT) | +2bp | |
| Fetus5 | CTTTTCCCAGGAGAAAATAATGAATGT-AAAGGAAGAGTGGTTCT | -1bp | |
| | CTTTTCCCAGGAGAAAATAATGAATGTCAAAGGAAGAGTGGTTCT (T) | +1bp | |
| Fetus6 | CTTTTCCCAGGAGAAAATAA----------AGGAAGAGTGGTTCT | -10bp | |
| | CTTTTCCCAGGAGAAAATAATGAA-------GGAAGAGTGGTTCT | -7bp | |
| Fetus7 | CTTTTCCCAGGAGAAAATAATGAATGTCAAAGGAAGAGTGGTTCT (GGAATAAT) | +3bp (-5bp, +8bp) | |
| CMAH | CAGGCGTGAGTAAGGTACGTGATCTGTTGGAAGACAGTGAGATTCAGATGAT | WT | SEQ ID NO: 25 |
| Fetus1 | CAGGCGTGAGTAAGGTACGTGATC--TTGGAAGACAGTGAGATTCAGATGAT | -2bp | |
| | CAGGCGTGAGTAAGGTACGTGATCTGTTGGAAGACAGTGAGATTCAGATGAT (T) | +1bp | |
| Fetus2 | CAGGCGTGAGTAAGGTACGTG-------GAAGACAGTGAGATTCAGATGAT | -6bp | |
| Fetus5 | CAGGCGTGAGTAAGGTACGTG------TTGGAAGACAGTGAGATTCAGATGAT | -5bp | |
| | CAGGCGTGAGTAAGGTACGTGA---GTTGGAAGACAGTGAGATTCAGATGAT | -3bp | |
| Fetus6 | CAGGCGTGAGTAAGGTACGTGATC-GTTGGAAGACAGTGAGATTCAGATGAT | -1bp | |
| | CAGGCGTGAGTCAGGTACGTGATCTGTTGGAAGACAGTGAGATTCAGATGAT (AC) | +1 (-1 bp, +2 bp) | |
| Fetus7 | CAGGCGTGAGTAAGGTACGTG------TTGGAAGACAGTGAGATTCAGATGAT | -5bp | |
| | CAGGCGTGAGTAAGGTACGTGAT---------------TCAGATGAT | -20bp | |

FIG. 9B

SEQUENCE LISTING

```
<160> NUMBER OF SEQ ID NOS: 25

<210> SEQ ID NO 1
<211> LENGTH: 35
<212> TYPE: DNA
<213> ORGANISM: Sus scrofa

<400> SEQUENCE: 1
aaactcctga actacaaggc tcggctggtg aagga                35

<210> SEQ ID NO 2
<211> LENGTH: 41
<212> TYPE: DNA
<213> ORGANISM: Sus scrofa
```

-continued

```
<400> SEQUENCE: 2
gtcatctttt acatcatggt ggatgatatc tccaggatgc c        41

<210> SEQ ID NO 3
<211> LENGTH: 22
<212> TYPE: DNA
<213> ORGANISM: Artificial Sequence
<220> FEATURE:
<223> OTHER INFORMATION: ZFN-CMAH-F Primer

<400> SEQUENCE: 3
ggacctgctt tatcttgctc gc                             22

<210> SEQ ID NO 4
<211> LENGTH: 22
<212> TYPE: DNA
<213> ORGANISM: Artificial Sequence
<220> FEATURE:
<223> OTHER INFORMATION: ZFN-CMAH-R Primer

<400> SEQUENCE: 4
ccatacttgt ctgctgggtg gg                             22

<210> SEQ ID NO 5
<211> LENGTH: 19
<212> TYPE: DNA
<213> ORGANISM: Artificial Sequence
<220> FEATURE:
<223> OTHER INFORMATION: CMAH-S1 Primer

<400> SEQUENCE: 5
ccaaaccctg tcattccag                                 19

<210> SEQ ID NO 6
<211> LENGTH: 20
<212> TYPE: DNA
<213> ORGANISM: Artificial Sequence
<220> FEATURE:
<223> OTHER INFORMATION: GGTA1-F Primer

<400> SEQUENCE: 6
ctagaaatcc cagaggttac                                20

<210> SEQ ID NO 7
<211> LENGTH: 20
<212> TYPE: DNA
<213> ORGANISM: Artificial Sequence
<220> FEATURE:
<223> OTHER INFORMATION: GGTA1-R Primer

<400> SEQUENCE: 7
tccttgtcct ggaggattcc                                20

<210> SEQ ID NO 8
<211> LENGTH: 25
<212> TYPE: DNA
<213> ORGANISM: Artificial Sequence
<220> FEATURE:
<223> OTHER INFORMATION: GGTA1-F Primer

<400> SEQUENCE: 8
ccttagtatc cttcccaacc cagac                          25

<210> SEQ ID NO 9
```

```
<211> LENGTH: 26
<212> TYPE: DNA
<213> ORGANISM: Artificial Sequence
<220> FEATURE:
<223> OTHER INFORMATION: GGTA1-R Primer

<400> SEQUENCE: 9
gctttcttta cggtgtcagt gaatcc                                          26

<210> SEQ ID NO 10
<211> LENGTH: 22
<212> TYPE: DNA
<213> ORGANISM: Artificial Sequence
<220> FEATURE:
<223> OTHER INFORMATION: CMAH-F primer

<400> SEQUENCE: 10
cttggaggtg atttgagttg gg                                              22

<210> SEQ ID NO 11
<211> LENGTH: 22
<212> TYPE: DNA
<213> ORGANISM: Artificial Sequence
<220> FEATURE:
<223> OTHER INFORMATION: CMAH-R primer

<400> SEQUENCE: 11
cattttcttc ggagttgagg gc                                              22

<210> SEQ ID NO 12
<211> LENGTH: 24
<212> TYPE: DNA
<213> ORGANISM: Artificial Sequence
<220> FEATURE:
<223> OTHER INFORMATION: GGTA1 forward sgRNA

<400> SEQUENCE: 12
caccgagaaa ataatgaatg tcaa                                            24

<210> SEQ ID NO 13
<211> LENGTH: 24
<212> TYPE: DNA
<213> ORGANISM: Artificial Sequence
<220> FEATURE:
<223> OTHER INFORMATION: GGTA1 reverse sgRNA

<400> SEQUENCE: 13
aaacttgaca ttcattattt tctc                                            24

<210> SEQ ID NO 14
<211> LENGTH: 24
<212> TYPE: DNA
<213> ORGANISM: Artificial Sequence
<220> FEATURE:
<223> OTHER INFORMATION: CMAH forward sgRNA

<400> SEQUENCE: 14
caccgagtaa ggtacgtgat ctgt                                            24

<210> SEQ ID NO 15
<211> LENGTH: 23
<212> TYPE: DNA
<213> ORGANISM: Artificial Sequence
<220> FEATURE:
<223> OTHER INFORMATION: CMAH reverse sgRNA
```

-continued

<400> SEQUENCE: 15
aaacacagat cacgtacctt act                                          23

<210> SEQ ID NO 16
<211> LENGTH: 35
<212> TYPE: DNA
<213> ORGANISM: Sus scrofa

<400> SEQUENCE: 16
aaactcctga actacaaggc tcggctggtg aagga                             35

<210> SEQ ID NO 17
<211> LENGTH: 39
<212> TYPE: DNA
<213> ORGANISM: Sus scrofa

<400> SEQUENCE: 17
aaactcctga actacaagga aggctcggct ggtgaagga                         39

<210> SEQ ID NO 18
<211> LENGTH: 41
<212> TYPE: DNA
<213> ORGANISM: Sus scrofa

<400> SEQUENCE: 18
gtcatctttt acatcatggt ggatgatatc tccaggatgc c                      41

<210> SEQ ID NO 19
<211> LENGTH: 38
<212> TYPE: DNA
<213> ORGANISM: Sus scrofa

<400> SEQUENCE: 19
gtcatctttt acatcatgaa tgatatctcc aggatgcc                          38

<210> SEQ ID NO 20
<211> LENGTH: 22
<212> TYPE: DNA
<213> ORGANISM: Sus scrofa

<400> SEQUENCE: 20
gagaaaataa tgaatgtcaa ag                                           22

<210> SEQ ID NO 21
<211> LENGTH: 23
<212> TYPE: DNA
<213> ORGANISM: Sus scrofa

<400> SEQUENCE: 21
gagaaaataa tgaatgttca aag                                          23

<210> SEQ ID NO 22
<211> LENGTH: 25
<212> TYPE: DNA
<213> ORGANISM: Sus scrofa

<400> SEQUENCE: 22
gagtaaggta cgtgatctgt tggaa                                        25

<210> SEQ ID NO 23
<211> LENGTH: 25
<212> TYPE: DNA

```
<213> ORGANISM: Sus scrofa
<220> FEATURE:
<221> NAME/KEY: misc_feature
<222> LOCATION: (21)..(21)
<223> OTHER INFORMATION: n is a, c, g, or t

<400> SEQUENCE: 23
gagtaaggta cgtgatctgt nggaa                                           25

<210> SEQ ID NO 24
<211> LENGTH: 45
<212> TYPE: DNA
<213> ORGANISM: Sus scrofa

<400> SEQUENCE: 24
cttttcccag gagaaaataa tgaatgtcaa aggaagagtg gttct                     45

<210> SEQ ID NO 25
<211> LENGTH: 52
<212> TYPE: DNA
<213> ORGANISM: Sus scrofa

<400> SEQUENCE: 25
caggcgtgag taaggtacgt gatctgttgg aagacagtga gattcagatg at             52
```

DOUBLE KNOCKOUT (GT/CMAH-KO) PIGS, ORGANS AND TISSUES

CROSS-REFERENCE TO RELATED APPLICATIONS

This application is a continuation application of U.S. patent application Ser. No. 15/848,870, filed Dec. 20, 2017, which is a divisional application of U.S. patent application Ser. No. 14/436,963, filed Apr. 20, 2015, now U.S. Pat. No. 9,888,674, which is the U.S. National Stage entry of PCT International Application No. PCT/US2013/066387, filed Oct. 23, 2013, which claims priority to U.S. patent application Ser. No. 13/804,365, filed Mar. 14, 2013, now abandoned, and claims the benefit of U.S. Provisional Patent Application No. 61/717,845, filed Oct. 24, 2012, each of which is incorporated herein by reference in its entirety for all purposes.

INCORPORATION OF SEQUENCE LISTING

The instant application contains a Sequence Listing which has been submitted via EFS-Web and is hereby incorporated by reference in its entirety. The ASCII copy is named 144578-00130_ST25 and is 5,000 bytes in size.

FIELD OF THE INVENTION

The present invention is generally in the field of xenotransplantation and genetic modification to produce transgenic animals, organs tissue, or cells suitable for transplantation into a human.

BACKGROUND

It is well known that transplants from one animal into another animal of the same species, such as human to human, are a routine treatment option for many serious conditions, including kidney, heart, lung, liver and other organ disease. However, it is also well known that there are not enough suitable organs available for transplant to meet current or expected clinical demands for organ transplants.

Xenotransplantation, the transplant of organs, tissue or cells from one animal into another animal of a different species, such as the transplantation of a pig organ into a human recipient, has the potential to eliminate the shortage of organs available for transplant, potentially helping hundreds of thousands of people worldwide. For instance, suitable organs for transplant from non-human donors, such as from a pig, could help keep seriously ill patients alive, either permanently or temporarily, until a suitable human organ is available for transplant.

While many mammalian animals may be suitable candidates for xenotransplantation, much of the current focus is on the pig. Using pig organs, tissue or cells for xenotransplantaion offers many advantages over other non-human mammalian donors. For instance, pigs are easily obtainable, they are inexpensive to breed and maintain, and, most importantly, many pig organs are similar to humans in size, shape and function.

However, xenotransplantation using standard, unmodified pig tissue into a human (or other primate) is accompanied by severe rejection of the transplanted tissue. The rejection may be a hyperacute rejection, an acute rejection or a chronic rejection. The hyperacute response to the pig antibodies present on the transplanted tissue is so strong that the transplant is typically damaged by the human immune system within minutes or hours of transplant into the human recipient.

Pig cells express α1,3 galactosyltransferase (αGal) and cytidine monophosphate-N-acetylneuraminic acid hydroxylase (CMAH), which are not found in human cells. The αGal enzyme produces the αGal epitope. CMAH converts the sialic acid N-acetylneuraminic acid (Neu5Ac) to N-glycolylneuraminic acid (Neu5Gc). Accordingly, when pig tissue is transplanted into a human, these epitopes elicit an antibody-mediated rejection from the human patient immediately following implantation. The antibodies are present in the patient's blood prior to implantation of the tissue, resulting in the intense and immediate rejection of the implanted tissue.

Many strategies have been employed to address the rejection caused by αGal and CMAH, including removing the genes encoding αGal or CMAH to prevent expression of the enzymes, modifying the genes encoding αGal or CMAH to reduce or limit expression of the enzymes or otherwise limiting the ability of the enzymes to trigger a rejection response. For instance, U.S. Pat. No. 7,547,816 to Day et al. describes a knockout pig with decreased expression of αGal as compared to wild-type pigs. U.S. Pat. Nos. 7,166,278 and 8,034,330 to Zhu et al. describe methods for making porcine organs for transplantation that are less likely to be subject to hyperacute rejection. However, progress in this field is critically dependent upon the development of the genetically modified pigs.

Unfortunately, developing homozygous knockout pigs is a slow process, requiring as long as three years using homologous recombination in fetal fibroblasts followed by somatic cell nuclear transfer (SCNT), and then breeding of heterozygous knockout animals. The development of new knockout pigs for xenotransplantation has been hampered by the lack of pluripotent stem cells, relying instead on the fetal fibroblast as the cell upon which genetic engineering was carried out. For instance, the production of the first live pigs lacking any functional expression of αGal (GTKO) was first reported in 2003. U.S. Pat. No. 7,795,493 to Phelps et al. describes a method for the production of a pig that lacks any expression of functional αGal.

Unfortunately, while the GTKO pig may have eliminated anti-αGal antibodies as a barrier to xenotransplantation, studies using GTKO cardiac and renal xenografts in baboons show that the GTKO organs still trigger an immunogenic response, resulting in rejection or damage to the transplanted organ. Baboons transplanted with GTKO kidneys and treated with two different immunosuppressive regimens died within 16 days of surgery. Chen et al. concluded "genetic depletion of Gal antigens does not provide a major benefit in xenograft survival" (Chen et al., 2005, *Nature Med.* 11(12): 1295-1298. Basnet et al examined the cytotoxic response of human serum to CMAH−/− mouse cells. Basnet et al. concluded "the anti-NeuGc Ab-mediated immune response may be significantly involved in graft loss in xenogeneic cell transplantation, but not in organ transplantation" (Basnet et al., 2010, *Xenotransplantation,* 17(6):440-448).

Thus, there is a need in the art for an improved, simple, replicable, efficient and standardized method of producing double knockout (αGAL and CMAH) pigs having no αGAL and CMAH expression (GT/CMAH-KO) as a source of human transplant material for organs, tissue and cells for human transplant recipients.

BRIEF SUMMARY

This disclosure relates generally to methods of making porcine organs, tissues or cells for transplantation into a human that do not express αGal and CMAH.

The present disclosure provides, in one embodiment, a knockout pig comprising disrupted α(1,3)-galactosyltransferase and CMAH genes, wherein expression of functional α(1,3)-galactosyltransferase and CMAH in the knockout pig is decreased as compared to a wild-type pig and when tissue from said pig is transplanted into a human, hyperacute rejection is decreased as compared to when tissue from a wild-type pig is transplanted into a human.

In another embodiment, the specification provides porcine organs, tissue or cells for transplantation into a human having reduced expression of αGal and CMAH on the porcine organs, tissue or cells.

In another embodiment, the specification provides a method for modifying a porcine organs, tissue or cells for transplantation into a human, the method comprising removing or reducing expression of αGal and CMAH on the porcine organs, tissue or cells. The porcine organs, tissue, or cells may be selected from the group consisting of red blood cells, skin, heart, livers, kidneys, lung, pancreas, thyroid, small bowel, and components thereof.

In another embodiment, the specification provides a method for making porcine organs, tissue or cells for transplantation into a human, the method comprising reducing expression of αGal and CMAH on the porcine organs, tissue or cells. The porcine organs, tissue, or cells may be selected from the group consisting of red blood cells, skin, heart, liver, kidneys, lung, pancreas, small bowel, and components thereof.

In another embodiment, the specification provides a knockout pig comprising disrupted α(1,3)-galactosyltransferase and CMAH genes, wherein expression of functional α(1,3)-galactosyltransferase and CMAH in the knockout pig is decreased as compared to a wild-type pig and wherein when tissue from a knockout pig is transplanted into a human, thrombocytopenia is decreased as compared to when tissue from a wild-type pig is transplanted into a human.

In another embodiment, the specification provides a knockout pig comprising disrupted α(1,3)-galactosyltransferase and CMAH genes, wherein expression of functional α(1,3)-galactosyltransferase and CMAH in the knockout pig is decreased as compared to a wild-type pig and wherein a liver from said pig exhibits reduced uptake of human platelets when said liver is exposed to said human platelets.

In another embodiment, the specification provides a method of increasing the duration of the period between when a human subject is identified as a subject in need of human liver transplant and when said human liver transplant occurs, said method comprising providing a liver from a knockout pig comprising disrupted α(1,3)-galactosyltransferase and CMAH genes, wherein expression of functional α(1,3)-galactosyltransferase and CMAH in the knockout pig is decreased as compared to a wild-type swine and surgically attaching said liver from said knockout pig to said human subject in a therapeutically effective manner. The liver from the knockout pig may be internal or external to the human subject, and may be directly or indirectly attached to the human subject.

In another embodiment, the specification provides a method of preparing organs, tissues, or cells for xenotransplantation into human patients with reduced rejection, the method comprising providing a transgenic pig as a source of transplant material wherein the transplant material is selected from the group consisting of organs, tissues, or cells, and wherein the pig masks or reduces the expression of at least two xenoreactive antigens on the transplant material. At least two xenoreactive antigens may be αGal and Neu5Gc.

In another embodiment, the specification provides a knockout pig comprising disrupted α(1,3)-galactosyltransferase and CMAH genes, wherein the disruption of said α(1,3)-galactosyltransferase gene is selected from the group of disruptions comprising a 3 base pair deletion adjacent to a G to A substitution, a single base pair deletion, a single base pair insertion, a six base pair deletion, a two base pair insertion, a ten base pair deletion, a seven base pair deletion, and an eight base pair substitution for a five base pair sequence; wherein the disruption of said CMAH gene is selected from the group of disruptions comprising a four base pair insertion, a two base pair deletion, a single base pair insertion, an eight base pair deletion, a five base pair deletion, a three base pair deletion, a two base pair substitution for a single base pair, and a twenty base pair deletion; and wherein expression of functional α(1,3)-galactosyltransferase and CMAH in said knockout pig is decreased as compared to a wild-type pig and when tissue from said knockout pig is transplanted into a human, a hyperacute rejection related symptom is improved as compared to when tissue from a wild-type pig is transplanted into a human.

In another embodiment, the specification provides a method of improving symptoms of hyperacute rejection in a patient comprising transplanting porcine organs, tissue or cells having reduced expression of αGal and CMAH on the porcine organs, tissue or cells into a human, wherein the symptoms of hyperacute rejection are improved as compared to tissue from a wild-type swine when transplanted into a human.

In another embodiment, the disclosure provides a cell culture reagent derived from a knockout pig comprising disrupted α(1,3)-galactosyltransferase and CMAH genes, wherein the disruption of said α(1,3)-galactosyltransferase gene is selected from the group of disruptions comprising a 3 base pair deletion adjacent to a G to A substitution, a single base pair deletion, a single base pair insertion, a six base pair deletion, a two base pair insertion, a ten base pair deletion, a seven base pair deletion, and an eight base pair substitution for a five base pair sequence; wherein the disruption of said CMAH gene is selected from the group of disruptions comprising a four base pair insertion, a two base pair deletion, a single base pair insertion, an eight base pair deletion, a five base pair deletion, a three base pair deletion, a two base pair substitution for a single base pair, and a twenty base pair deletion; and wherein expression of functional α(1,3)-galactosyltransferase and CMAH in said knockout pig is decreased as compared to a wild-type pig. A cell culture reagent may be selected from the group of cell culture reagents comprising cell culture media, cell culture serum, a cell culture additive and an isolated cell capable of proliferation.

In a further embodiment, the invention provides a method of producing a glycoprotein of interest comprising the step of incubating an isolated cell capable of expressing the glycoprotein of interest with a cell culture reagent derived from a knockout pig comprising disrupted α(1,3)-galactosyltransferase and CMAH genes, wherein the amount of Neu5Gc or αGal epitopes on the glycoprotein of interest is lower than the amount of Neu5Gc or αGal epitopes on the glycoprotein of interest when an isolated cell capable of expressing said glycoprotein of interest is incubated with a cell culture reagent derived from a wild-type pig. The glycoprotein of interest may be selected from the group comprising an antibody, growth factor, cytokine, hormone and clotting factor. In an aspect of the disclosure, the disruption of the α(1,3)-galactosyltransferase gene is selected from the group of disruptions comprising a 3 base pair deletion adjacent to a G to A substitution, a single base pair deletion, a single base pair insertion, a six base pair deletion, a two base pair insertion, a ten base pair deletion, a seven base pair deletion, and an eight base pair substitution for a five base pair sequence; the disruption of said CMAH gene is selected from the group of disruptions comprising a four base pair insertion, a two base pair deletion, a single base pair insertion, an eight base pair deletion, a five base pair deletion, a three base pair deletion, a two base pair substitution for a single base pair, and a twenty base pair deletion; and expression of the functional α(1,3) galactosyltransferase and CMAH in the knockout pig from which the cell culture reagent is derived is decreased as compared to a wild-type pig.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

The disclosure will be better understood and features, aspects and advantages other than those set forth above will become apparent when consideration is given to the following detailed description thereof. Such detailed description makes reference to the following drawings.

FIG. 2A presents a photographic image of harvested double-KO fetuses.

FIG. 2B provides representative electropherograms of the mutations found in the CMAH gene in the double knockout fetuses. SEQ ID NO:16 provides a portion of the wild-type CMAH gene sequence; SEQ ID NO:17 provides a disrupted version of the CMAH sequence. Mutations are underlined while the DNA binding sites of the ZFN are italicized. FIG. 2B also provides representative electropherograms of the mutations found in the GGTA1 gene in the double knockout fetuses. SEQ ID NO:18 provides a portion of the wild-type GGTA1 gene sequence; SEQ ID NO:19 provides a disrupted version of the GGTA1 gene sequence. Mutations are underlined while the DNA binding sites of the ZFN are italicized.

FIG. 2C presents data obtained from flow cytometric analysis of red blood cells (RBC) obtained from six month old wild-type piglets (WT), six-month-old GGTA1-KO (GGTA1-KO) piglets, double-KO fetuses and adult humans showing cells stained with an antibody recognizing Neu5GC. Panel E presents data obtained from flow cytometric analysis of red blood cells (RBC) obtained from six month old wild-type piglets (WT), six-month-old GGTA1-KO (GGTA1-KO) piglets, double-KO fetuses and adult humans showing cells stained with fluorescently labeled IB4 lectin to measure the level of the Gal epitopes. Unstained RBC were used as negative controls for IB4 lectin staining and an isotype matched control was used for Neu5Gc staining. Some negative control histograms are difficult to see because of significant overlap with the experimental group.

FIG. 4A and FIG. 4B provide confocal micrographs of tissues from wild type (WT), single (GGTA1-KO) and CMAH-/-/GGTA-/-(double-KO) pigs. DAPI staining of nuclei may be visible. Heart, kidney and liver tissues were stained with anti-Neu5Gc antibody in the micrographs of panel A. Limited staining of Neu5Gc occurs in tissues from double-KO pigs. Heart, kidney and liver tissues were stained with IB4 lectin in the micrographs of panel B. Limited IB4 binding occurs in tissues from GGTA1-KO and double-KO pigs.

FIG. 4C presents results obtained from flow cytometry analysis of peripheral blood mononuclear cells (PBMC). Traces were obtained from cells labeled with anti-Neu5Gc antibody (left column) and IB4 lectin (right column). Unstained PBMC were the negative controls for IB4 lectin; an isotype negative control was used in the anti-Neu5Gc staining. Negative controls are shown (*) but are difficult to see in some panels because of significant overlap with the experimental group.

FIG. 5A shows IgG (A) and IgM (B) histograms of a representative sample (Subject 5) of randomly chosen normal human serum against GGTA1-KO or double-KO cells. Bar graphs of FIG. 5A show the mean fluorescent intensities (MFI) of IgM or IgG binding to peripheral blood monocytes (PBMCs). The results of testing ten unique human subjects are shown.

FIG. 5B illustrates example curves (Subject 3) for antibody-mediated complement-dependent cytotoxicity of normal human serum against GGTA1-KO and double KOPBMCs. Percent cytotoxicity for each serum tested (2.0% final concentration) is shown.

FIG. 7A provides results of flow cytometry analysis of the α-Gal epitope on LDCs that survived IB4 lectin counter-selection. Also shown are unlabeled LDC and labeled, non-transfected LDC. In the particular example shown, 91.7% of the selected cells were free of the α-Gal epitope.

FIG. 7B provides an electropherogram of mutations found in Crispr-targeted GGTA1 and CMAH regions. The wild-type sequence of a portion of each targeted region is shown above the sequencing results as SEQ ID NO:20 for the wild-type GGTA1 segment, as SEQ ID NO:21 for a disrupted or mutant GGTA1 segment, as SEQ ID NO:22 for the wild-type CMAH segment, and as SEQ ID NO:23 for a disrupted or mutant CMAH segment. The top electropherogram is a portion of the GGTA1 gene; the bottom electropherogram is a portion of the CMAH gene.

FIGS. 9A-9C provides panels pertaining to generation of CMAH/αGal DKO fetuses from CMAH-CrispR and αGal-CrispR transfected LDC.

FIG. 9A provides a photograph of 10 fetuses harvested at day 32 of gestation after SCNT of Crispr-transfected LDC that survived IB4 counterselection and implantation of resulting embryos in recipient sows. DNA sequencing analysis of the GGTA1 and CMAH target regions was performed on each fetus. For GGTA1, seven fetuses contained biallelic mutations, one fetus contained a monoallelic mutation, and two fetuses were wild-type. For CMAH, five fetuses contained biallelic mutations, one fetus contained a monoallelic mutation, and four fetuses were wild-type.

FIG. 9B provides the results of DNA sequencing analysis of the targeted GGTA1 and CMAH regions of five DKO fetuses with mutations in both alleles of both CMAH and GGTA1. If the two alleles have different mutations in a particular fetus, the sequence of both alleles is shown. If the two alleles of a fetus have the same mutation, the sequence is only shown once. The net change in nucleotide number is indicated to the right of the sequences. The wild-type sequence of the relevant portions of the GGTA1 and CMAH genes is shown above the fetal sequences. The relevant portion of the wildtype GGTA1 gene, including that set forth in SEQ ID NO:20, is represented as SEQ ID NO:24. The relevant portion of the wild-type CMAH gene, including that set forth in SEQ ID NO:21, is represented as SEQ ID NO:25. Fetal fibroblasts were derived from fetus 7.

FIG. 9C provides data from flow cytometry analysis of αGal and Neu5Gc on double knockout (DKO) and wild-type (WT) fetal fibroblasts. Unlabeled DKO and WT cells were also analyzed. The upper trace shows αGal results; the lower trace shows Neu5Gc results.

FIG. 10A illustrates data from an isotype control.

FIG. 10B provides Neu5Gc data. Cells grown in the CMAH deficient serum show lower anti-Neu5Gc antibody binding than cells grown in FBS.

FIG. 11A The upper panel provides flow cytometry results obtained from isotype control analysis of a CMAH/αGal DKO cell line (CMAH/Gal KO Fibroblast cell line) and αGal1 single knockout kidney cells (GGTA KO renal cells).

FIG. 11B The lower panel provides flow cytometry results of Neu5Gc on a CMAH/αGal DKO cell line (CMAH/Gal KO Fibroblast cell line) grown in culture media supplemented with CMAH/αGal derived serum and a GGTA-1 kidney cell line grown in culture media supplemented with FBS.

DETAILED DESCRIPTION OF THE INVENTION

Figure 1:
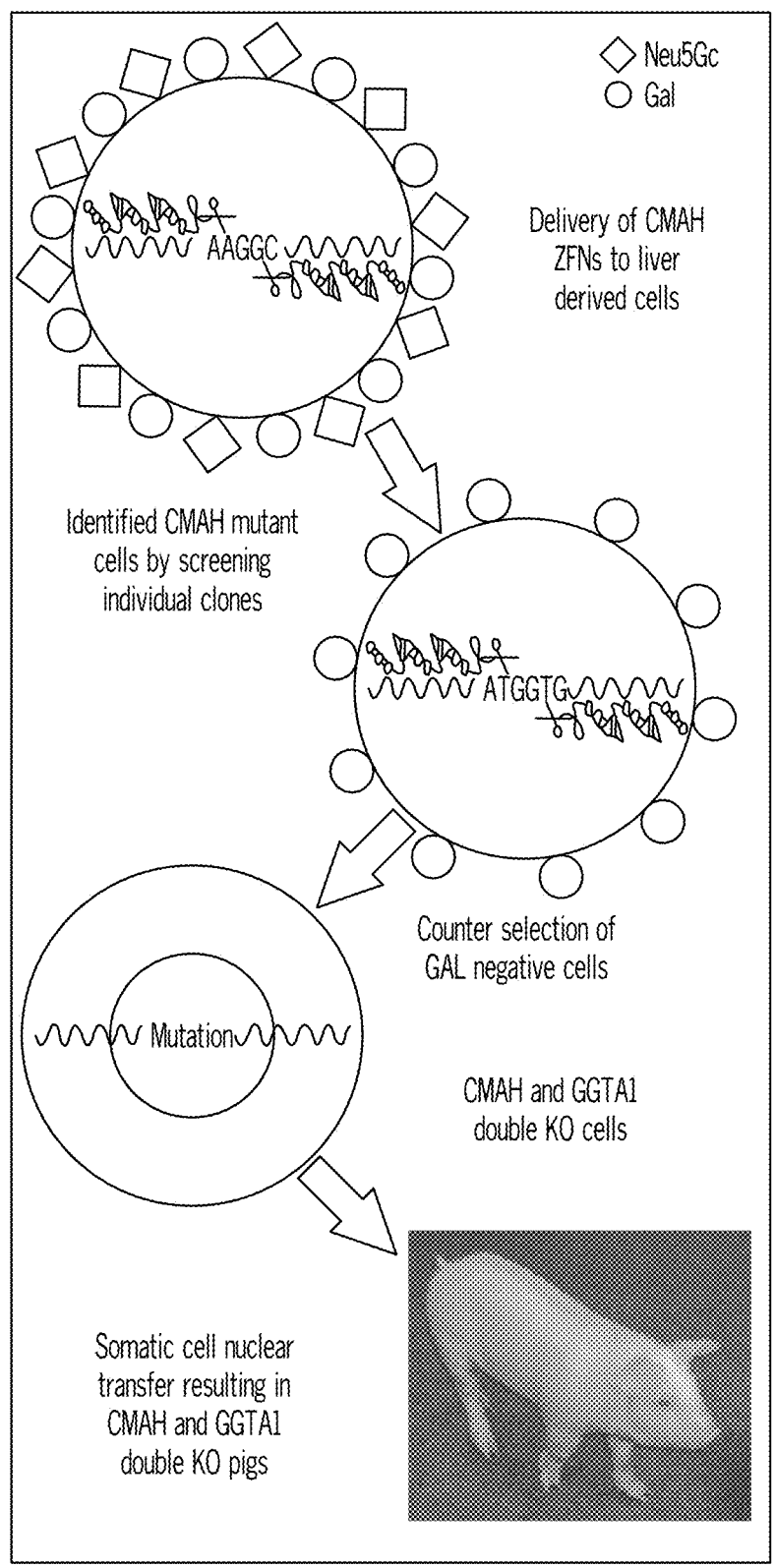
FIG. 1 depicts a schematic of a protocol used to develop the double knock-out CMAH/GGTA1-pigs. Step a) shows the delivery of CMAH ZFNs to liver derived cells. Step b) illustrates identified CMAH mutant cells by screening individual clones. Step c) illustrates the delivery of GGTA1 ZFNs to CMAH KO cells. Step d) illustrates the counter-selection of Gal negative cells. Step e) illustrates CMAH and GGTA1 double KO cells. Step f) illustrates somatic cell nuclear transfer (SCNT) resulting in CMAH and GGTA1 double KO cells.

The present invention provides pigs and porcine organs, tissues or cells for transplantation into a human that do not express αGal and CMAH and methods of making the same. In one embodiment, the invention provides a knockout pig comprising disrupted α(1,3)-galactosyltransferase and CMAH genes, wherein expression of functional α(1,3)-galactosyltransferase and CMAH in the knockout pig is decreased as compared to a wild-type pig and when tissue from said pig is transplanted into a human, hyperacute rejection is decreased as compared to when tissue from a wild-type pig is transplanted into a human.

I. In General.

In the specification and in the claims, the terms "including" and "comprising" are open-ended terms and should be interpreted to mean "including, but not limited to . . ." These terms encompass the more restrictive terms "consisting essentially of" and "consisting of."

As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention.

The present invention provides transgenic animals suitable for use in xenotransplantation and methods of producing mammals suitable for use in xenotransplantation. Specifically, the present invention describes the production of homozygous double knockout pigs lacking any functional expression of alpha 1,3 galactosyltransferase (αGAL) and CMAH. In one embodiment, the production of pigs with copies of the αGal and CMAH genes knocked out prior to somatic cell nuclear transfer (SCNT) is described. The time to create a two gene homozygous knockout took less than 10 months, significantly reducing the time required to create new pigs to speed up the progress of xenotransplantation research.

The term "knockout mammal" refers to a transgenic mammal wherein a given gene has been altered, removed or disrupted. By a "double knockout" we mean a transgenic mammal wherein two genes have been altered, removed or disrupted. It is to be emphasized that the term is intended to include all progeny generations. Thus, the founder animal and all F1, F2, F3, and so on, progeny thereof are included. In principle, knockout animals may have one or both copies of the gene sequence of interest disrupted. In the latter case, in which a homozygous disruption is present, the mutation is termed a "null" mutation. In the case where only one copy of the nucleic acid sequence of interest is disrupted, the knockout animal is termed a "heterozygous knockout animal". The knockout animals of the invention are typically homozygous for disruptions of both genes being targeted.

The term "chimera," "mosaic" or "chimeric mammal" refers to a transgenic mammal with a knockout in some of its genome-containing cells.

The term "heterozygote" or "heterozygotic mammal" refers to a transgenic mammal with a disruption on one of a chromosome pair in all of its genome containing cells.

The term "homozygote" or "homozygotic mammal" refers to a transgenic mammal with a disruption on both members of a chromosome pair in all of its genome-containing cells.

A "non-human mammal" of the invention includes mammals such as rodents, sheep, dogs, ovine such as lamb, bovine such as beef cattle and milk cows, and swine such as pigs and hogs. Although the invention uses a typical non-human animal (e.g., porcine), other mammals can similarly be genetically modified using the methods and compositions of the invention.

A "mutation" is a detectable change in the genetic material in the animal, which is transmitted to the animal's progeny. A mutation is usually a change in one or more deoxyribonucleotides, such as, for example, adding, deleting, inverting, or substituting nucleotides.

By "pig" we mean any pig known to the art, including a wild pig, a domestic pig, mini pigs, a *Sus scrofa* pig, a *Sus scrofa domesticus* pig, as well as inbred pigs. Without limitation, the pig can be selected from the group consisting of, for example, Landrace, Yorkshire, Hampshire, Duroc, Chinese Meishan, Chester White, Berkshire Goettingen, Landrace/York/Chester White, Yucatan, Bama Xiang Zhu, Wuzhishan, Xi Shuang Banna, and Pietrain pigs. Porcine organs, tissue or cells are organs, tissue or cells from a pig.

Transgenic Animals. The present invention provides a transgenic animal lacking any expression of functional αGal and CMAH genes. The animal can be any mammal suitable for xenotransplantation. In a specific embodiment, the animal is a pig. "CMAH/αGAL double knockouts", "CMAH/αGAL DKO", "CMAH/αGal", "CMAH/αGal DKO", "CMAH$^{-/-}$/GAL$^{-/-}$", "αGal/CMAH DKOs", "αGAL/CMAH double knockouts", "GGTA1/CMAH DKO", "GT1/CMAH DKO", "GGTA1$^{-/-}$/CMAH$^{-/-}$", "GGT1$^{-/-}$/CMAH$^{-/-}$", "CMAH/GGTA DKO", "GT/CMAH-KO", "GGTA1/CMAH KO", "DKO (αGal/CMAH)", "DKO (αGAL & CMAH)", "CMAH-/αGal-", "αGal-/CMAH-", "CMAH-/αGAL-" and variants thereof refer to animals, cells, or tissues that lack expression of functional alpha 1,3 galactosyltransferase and cytidine monophosphate-N-acetylneuraminic acid hydroxylase.

Transgenic Material. In another embodiment, the invention provides organs, tissue and/or cells from animals lacking any expression of functional αGal and CMAH for use as xenografts. The tissues from animals lacking any functional expression of the αGal and CMAH gene can be obtained from a prenatal, neonatal, immature, or fully mature animal, such as a porcine, bovine or ovine. The organ may be used as a temporary or permanent organ replacement for a patient in need of an organ transplant. Any porcine organ can be used, including but not limited to the brain, heart, lungs, eye, stomach, pancreas, kidneys, liver, intestines, uterus, bladder, skin, hair, nails, ears, glands, nose, mouth, lips, spleen, gums, teeth, tongue, salivary glands, tonsils, pharynx, esophagus, large intestine, small intestine, rectum, anus, thyroid gland, thymus gland, bones, cartilage, tendons, ligaments, suprarenal capsule, skeletal muscles, smooth muscles, blood vessels, blood, spinal cord, trachea, ureters, urethra, hypothalamus, pituitary, pylorus, adrenal glands, ovaries, oviducts, vagina, mammary glands, testes, seminal vesicles, penis, lymph, lymph nodes and lymph vessels.

In another embodiment, the invention provides non-human tissues that are useful for xenotransplantation. In one embodiment, the non-human tissue is porcine tissue. Any porcine tissue can be used, including but not limited to epithelium, connective tissue, blood, bone, cartilage, muscle, nerve, adenoid, adipose, areolar, bone, brown adipose, cancellous, muscle, cartilaginous, cavernous, chondroid, chromaffin, dartoic, elastic, epithelial, fatty, fibrohyaline, fibrous, Gamgee, gelatinous, granulation, gut-associated lymphoid, skeletal muscle, Haller's vascular, indifferent, interstitial, investing, islet, lymphatic, lymphoid, mesenchymal, mesonephric, multilocular adipose, mucous connective, myeloid, nasion soft, nephrogenic, nodal, osteoid, osseous, osteogenic, retiform, periapical, reticular, rubber, smooth muscle, hard hemopoietic, and subcutaneous tissue.

The invention also provides cells and cell lines from porcine animals that lack expression of functional αGal and CMAH. In one embodiment, these cells or cell lines can be used for xenotransplantation. Cells from any porcine tissue or organ can be used, including, but not limited to: epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, Islets of Langerhans cells, pancreatic insulin secreting cells, pancreatic alpha-2 cells, pancreatic beta cells, pancreatic alpha-1 cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, dopamiergic cells, squamous epithelial cells, osteocytes, osteoblasts, osteoclasts, dopaminergic cells, embryonic stem cells, fibroblasts and fetal fibroblasts.

Nonviable derivatives include tissues stripped of viable cells by enzymatic or chemical treatment these tissue derivatives can be further processed through crosslinking or other chemical treatments prior to use in transplantation. In a preferred embodiment, the derivatives include extracellular matrix derived from a variety of tissues, including skin, bone, urinary, bladder or organ submucosal tissues. In addition, tendons, joints, and bones stripped of viable tissue to including but not limited to heart valves and other nonviable tissues as medical devices are provided. In an embodiment, serum or medium suitable for cell culture and isolated from a knockout pig of the invention are provided. Components of porcine knockout organs, tissues or cells are also provided. Components may also be modified through any means known in the art including but not limited to crosslinking and aldehyde crosslinking. Components may vary depending on the larger organ or tissue from which the component is obtained. Skin components may include but are not limited to stripped skin, collagen, epithelial cells, fibroblasts and dermis. Bone components may include but are not limited to collagen and extracellular matrix. Heart components may include but are not limited to valves and valve tissue.

Expression of a gene product is decreased when total expression of the gene product is decreased, a gene product of an altered size is produced or when the gene product exhibits an altered functionality. Thus if a gene expresses a wild-type amount of product but the product has an altered enzymatic activity, altered size, altered cellular localization pattern, altered receptor-ligand binding or other altered activity, expression of that gene product is considered decreased. Expression may be analyzed by any means known in the art including, but not limited to, RT-PCR, Western blots, Northern blots, microarray analysis, immunoprecipitation, radiological assays, polypeptide purification, spectrophotometric analysis, Coomassie staining of acrylamide gels, ELISAs, 2-D gel electrophoresis, in situ hybridization, chemiluminescence, silver staining, enzymatic assays, ponceau S staining, multiplex RT-PCR, immunohistochemical assays, radioimmunoassay, colorimetric assays, immunoradiometric assays, positron emission tomography, fluorometric assays, fluorescence activated cell sorter staining of permeablized cells, radioimunnosorbent assays, real-time PCR, hybridization assays, sandwich immunoassays, flow cytometry, SAGE, differential amplification or electronic analysis. Expression may be analyzed directly or indirectly. Indirect expression analysis may include but is not limited to, analyzing levels of a product catalyzed by an enzyme to evaluate expression of the enzyme. See for example, Ausubel et al, eds (2013) Current Protocols in Molecular Biology, Wiley-Interscience, New York, N.Y. and Coligan et al (2013) Current Protocols in Protein Science, Wiley-Interscience New York, N.Y. Gene expression assays for porcine ASGR1 are commercially available (Applied Biosystems™, Carlsbad Calif.).

"As compared to" is intended encompass comparing something to a similar but different thing, such as comparing a data point obtained from an experiment with a knockout pig to a data point obtained from a similar experiment with a wildtype pig. The word "comparing" is intended to encompass examining character, qualities, values, quantities, or ratios in order to discover resemblances or differences between that which is being compared. Comparing may reveal a significant difference in that which is being compared. By "significant difference" is intended a statistically significant difference in results obtained for multiple groups such as the results for material from a knockout pig and material from a wild-type pig. Generally statistical significance is assessed by a statistical significance test such as but not limited to the student's t-test, Chi-square, one-tailed t-test, two-tailed t-test, ANOVA, Dunett's post hoc test, Fisher's test and z-test. A significant difference between two results may be results with a $p<0.1$, $p<0.05$, $p<0.04$, $p<0.03$, $p<0.02$, $p<0.01$ or greater.

The word "isolated" is intended to encompass an entity that is physically separated from another entity or group. An isolated cell is physically separated from another group of cells. Examples of a group of cells include, but are not limited to, a developing cell mass, a cell culture, a cell line, a tissue, and an animal. The word "isolating" is intended to encompass physically separating an entity from another entity or group. Examples include physically separating a cell from other cells, physically separating a cell component from the remainder of the cell and physically separating tissue or organ from an animal. An isolated cell or cell component is separated by 10%, 15%, 20%, 25%, 30%, 35%, 40%, 45%, 50%, 55%, 60%, 65%, 70%, 75%, 80%, 85%, 90%, 95%, 96%, 97%, 98%, 99%, up to 100% of other naturally occurring cells or cell components. Methods for isolating one or more cells from another group of cells are known in the art. See for example Freshney (ED) *Culture of Animal Cells: a manual of basic techniques* (3$^{rd}$ Ed.) 1994, Wiley-Liss; Spector et al (Eds)(1998) *Cells: a Laboratory Manual*(vol. 1) Cold Spring Harbor Laboratory Press and Darling et al (1994) *Animal Cells: culture and media* John Wiley & Sons. Methods of isolating a tissue or an organ from an animal are known in the art and vary depending on the tissue or organ to be isolated and the desired method of transplanting the tissue or organ.

A "skin related product" encompasses products isolated from skin and products intended for use with skin. Skin related products isolated from skin or other tissues may be modified before use with skin. Skin related products include but are not limited to replacement dressings, burn coverings, dermal products, replacement dermis, dermal fibroblasts, collagen, chondroitin, connective tissue, keratinocytes, cell-free xenodermis, cell-free pig dermis, composite skin substitutes and epidermis and temporary wound coverings. See for example Matou-Kovd et al (1994) *Ann Med Burn Club* 7:143, herein incorporated by reference in its entirety.

"Xenotransplantation" encompasses any procedure that involves the transplantation, implantation or infusion of cells, tissues or organs into a recipient subject from a different species. Xenotransplantation in which the recipient is a human is particularly envisioned. Thus xenotransplantation includes but is not limited to vascularized xenotransplant, partially vascularized xenotransplant, unvascularized xenotransplant, xenodressings, xenobandages, and xenostructures.

In another embodiment, the invention provides a method of improving a hyperacute rejection related symptom in a patient comprising transplanting porcine organs, tissue or cells having reduced expression of αGal and Neu5Gc on the porcine organs, tissue or cells into a human, wherein the hyperacute rejection related symptoms are improved as compared to when tissue from a wild-type swine is transplanted into a human. By "improving", "bettering", "ameliorating", "enhancing", and "helping" is intended advancing or making progress in what is desirable. It is also envisioned that improving a hyperacute rejection related symptom may encompass a decrease, lessening, or diminishing of an undesirable symptom. By "hyperacute rejection" we mean rejection of the transplanted material or tissue occurring or beginning within the first 24 hours post-transplant involving one or more mechanisms of rejection. Hyperacute rejection encompasses but is not limited to "acute humoral rejection" and "antibody mediated rejection".

"Hyperacute rejection related symptom" is intended to encompass any symptom known to the field as related to or caused by hyperacute rejection. It is recognized that hyperacute rejection related symptoms may vary depending upon the type of organ, tissue or cell that was transplanted. Hyperacute rejection related symptoms may include, but are not limited to, thrombotic occlusion, hemorrhage of the graft vasculature, neutrophil influx, ischemia, mottling, cyanosis, edema, organ failure, reduced organ function, necrosis, glomerular capillary thrombosis, lack of function, hemolysis, fever, clotting, decreased bile production, asthenia, hypotension, oliguria, coagulopathy, elevated serum aminotransferase levels, elevated alkaline phosphatase levels, jaundice, lethargy, acidosis and hyperbilirubenemia and thrombocytopenia.

Thrombocytopenia is a quantity of platelets below the normal range of 140,000 to 440,000/µl. Thrombocytopenia related symptoms include, but are not limited to, internal hemorrhage, intracranial bleeding, hematuria, hematemesis, bleeding gums, abdominal distension, melena, prolonged menstruation, epistaxis, ecchymosis, petechiae or purpura. Uptake of human platelets by pig livers contributes to the development of thrombocytopenia in xenograft recipients.

Platelets, also known as thrombocytes, are enucleate fragments of megakaryocytes involved in blood coagulation, hemostasis and blood thrombus formation. Human platelets are routinely isolated through a variety of methods including, but not limited to, platelet apheresis, plateletpheresis and ultracentrifugation.

The phrase "platelet uptake" is intended to encompass the incorporation of a platelet into a liver or liver cell. While not being limited by mechanism, such uptake may occur through a phagocytic process. Platelet uptake may be monitored by any platelet uptake monitoring assay known in the art. Platelet uptake monitoring assays include, but are not limited to immunological methods, western blots, immunoblotting, microscopy, confocal microscopy, transmission electron microscopy and phagosome isolation. It is recognized that the appropriate platelet uptake monitoring assay may depend upon the type of label used. Platelet uptake may be measured as a percentage of total platelets absorbed, percentage of total platelets not absorbed, a ratio of absorbed to unabsorbed platelets, percentage of cells absorbing at least one platelet, percentage of cells not absorbing a platelet, or number of platelets absorbed per cell. It is recognized that platelet uptake by more than one cell type may contribute to the total platelet uptake of the liver. Total platelet uptake by an animal liver may include platelet uptake by liver sinusoidal endothelial cells, platelet uptake by Kupffer cells, platelet uptake by LSECs and Kupffer cells and platelet uptake by additional cell types. It is recognized that platelet uptake by different cell types may contribute similar or disparate fractions of the total platelet uptake by a liver. Thus an alteration, inhibition, reduction, decrease, or lowering of platelet uptake by a liver comprises an alteration, inhibition, reduction, decrease, or lowering of platelet uptake by one or more liver cell types.

The word "providing" is intended to encompass preparing, procuring, getting ready, making ready, supplying or furnishing. It is recognized that methods of providing a cell may differ from methods of providing a subject and that methods of providing a liver may differ from methods of providing a pig.

In an embodiment, a cell culture reagent derived from a transgenic pig comprising disrupted α(1,3)-galactosyltransferase and CMAH genes is provided. Cell culture reagents are reagents utilized for tissue culture, in vitro tissue culture, microfluidic tissue culture, cell culture or other means of growing isolated cells or cell lines. Cell culture reagents may include but are not limited to cell culture media, cell culture serum, a cell culture additive, a feeder cell, and an isolated cell capable of proliferation. By an "isolated cell capable of proliferation" is intended a cell isolated or partially isolated from other cell types or other cells wherein the cell is capable of proliferating, dividing, or multiplying into at least one additional clonal cell.

Cells grown in culture may synthesize or metabolically incorporate antigenic epitopes into glycoproteins secreted by the cultured cell. The antigenic epitopes may result in increased binding by human antibodies and decreased efficacy of the glycoprotein. See Ghaderi et al, 2010 *Nature Biotechnology* 28(8):863-867, herein incorporated by reference in its entirety. Growing the producing cell in a cell culture reagent with less αGal or Neu5Gc may reduce the amount of αGal, Neu5Gc, or both αGal and Neu5Gc epitopes on the glycoprotein of interest. Glycoproteins of interest may include any glycoprotein, particularly glycoproteins intended for use in human subjects such as but not limited to, an antibody, growth factor, cytokine, hormone, or clotting factor.

In summary, xenoantigens αGal and Neu5Gc were eliminated in transgenic pigs by genetic modification. Double knockout pigs (GT/CMAH-KO) were produced within 5-10 months or less.

In embodiments of the present invention, tissues are provided in which both the αGal and CMAH genes are rendered inactive, such that the resultant αGal and CMAH products can no longer generate alpha 1,3-galactosyl epitopes or Neu5Gc on the cell surface. In an alternative embodiment, the αGal and CMAH genes can be inactivated in such a way that no transcription of the gene occurs.

In yet another aspect, the present invention provides a method for producing viable pigs lacking any functional expression of αGal and CMAH. In one embodiment, the pigs are produced as described below. Methods of making transgenic pigs, and the challenges thereto, are discussed in Galli et al. 2010 Xenotransplantation, 17(6) p. 397-410, incorporated by reference herein for all purposes. The methods and cell cultures of the invention are further detailed below.

EXAMPLES

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1. Design of Zinc Finger Nucleases (ZFN)

A pair of ZFN were designed to bind and cleave the sequence of porcine CMAH exon 9 (SEQ ID NO: 1-AAACTCCTGAACTACAAGGCTCGGCTGGT-GAAGGA) beginning at position 1,341 of Ensemble transcript ENSSSCT00000001195. Another pair of ZFN were designed to bind and cleave the region of GGTA1 exon 8 (SEQ ID NO: 2-GTCATCTTTTACATCATGGTGGATGA-TATCTCCAGGATGCC) beginning at position 1165 of Ensemble transcript ENSSSCT00000006069. The ZFN activities were validated in yeast (Sigma-Aldrich, St. Louis, Mo.). Additional detail regarding the ZFN of the present invention can be found in Li et al., Journal of Surgical Research, (2012)E1-E7 Epub 2012 July 3, which is incorporated by reference herein for all purposes.

Example 2. Cell Culture and Transfection of Porcine Liver Derived Cells

Porcine adult liver derived cells (LDC) were isolated with modifications from the method described in Li et al, 2010 Cell Reprogram. 12:599. Isolated LDC were cultured in a combination stem cell media (SCM) (α-MEM:EGM-MV 3:1) (Invitrogen/Lonza, Switzerland) supplemented with 10% fetal bovine serum (FBS) (Hyclone, Logan, Utah), 10% horse serum (Invitrogen, Carlsbad, Calif.), 12 mM HEPES, and 1% Pen/Strep (Invitrogen) as described in Li et al. 2012 JSR Epub 2012 July 3. A commercial porcine strain (Landrace/York/Chester White) was used as the source of the LDC. Neon transfection system was used according to the manufacturer's instruction (Invitrogen).

Briefly, LDC were harvested by trypsin digestion, washed with calcium and magnesium free Dulbecco's phosphate buffered saline (DPBS) (Invitrogen) and centrifuged. $10^6$ cells were suspended in 120 µl of resuspension buffer (Invitrogen) containing 2 µgs of each CMAH ZFN plasmid. pEGFP-N 1 (Clonetech, Mountain View, Calif.) was used as a control to measure transfection efficiency as well as ZFN activity. Cells were electroporated at 1300 V, 30 msec for 1 pulse.

Then cells were transferred in SCM without antibiotics and plated onto collagen I coated plates. Cells were cultured with 5% $CO_2$ and 10% 02 at 30° C. for 3 days and 37° C. for 2 days.

Example 3. Surveyor Mutation Detection Assay (CEL I Assay)

ZFN-induced mutation was detected using the Surveyor Mutation Detection kit (Transgenomic, Omaha, Nebr.). At day 5 post-transfection, genomic DNA from ZFN-treated and control plasmid pEGFP-N1 treated cells was extracted and PCR was performed using primers ZFN-CMAH-F (SEQ ID NO: 3-5' GGACCTGCTTTATCTTGCTCGC 3'), ZFN-CMAH-R (SEQ ID NO: 4-5' CCAT-ACTTGTCTGCTGGGTGGG 3'). Pwo SuperYield DNA Polymerase, dNTPack (Roche, Indianapolis, Ind.) was used and the PCR conditions were as follows: 94° C., 2 minutes; 94° C., 15 seconds, 55° C., 30 seconds and 68° C., 50 seconds for 15 cycles; 94° C., 15 seconds, 5 5° C., 30 seconds and 68° C., 50 seconds with additional 5 seconds for each cycle, for 25 cycles and a final extension step of 68° C. for 5 minutes.

PCR product was denatured and annealed using the following program on a MyCycler (Bio-Rad): 95° C., 10 minutes; 95° C. to 85° C., −2° C./second; 85° C. to 25° C., −0.1° C./second. 200-400 ng of PCR product was digested with 1 µl of Nuclease S and 1 µl of enhancer (Transgenomic, Omaha, Nebr.) at 42° C. for 40 minutes. The product was separated on a 10% polyacrylamide gel and stained with SYBR Safe to assess ZFN-induced mutations.

Example 4. Screening CMAH Mutant Cells

ZFN-treated cells were plated at 1 cell/well in ten 96-well plates coated with collagen I (BD, Franklin Lakes N.J.). After 14 days, single cell clones became evident. Cells were expanded to 48-well plate. Some cells were harvested for mutation screening. PCR was performed as described above herein. PCR products were resolved on a 0.8% agarose gel and purified by QlAquick Gel Extraction Kit (Qiagen). Primer CMAH-S1 (SEQ ID NO: 5-5' CCAAACCCTGT-CATTCCAG 3') was used to sequence the ZFN targeted CMAH region. A clone with an identical mutation in both CMAH gene copies was identified.

Disruption of GGTA 1 gene on CMAH mutant cells and counter selection of α-Gal-cells $10^6$ of CMAH mutant cells were transfected with 2 µgs of each GGTA1 ZFN plasmid as described below herein. αGal-cells were isolated by the counter selection method described below herein.

Example 5. Counter Selection of αGal-Cells

CMAH deficient LDC were treated with zinc finger plasmids targeting porcine 1,3 αGal. Alternatively LDC were transfected with Crispr CMAH sgRNA expression plasmids and GGTA1 sgRNA expression plasmids and grown for 48 hours as described elsewhere herein. The cells were harvested, washed and counted. A total of 2.3×10⁶ cells were incubated with 5 µg of biotin-conjugated *Griffonia simplicifolia* isolectin IB4 (IB4 lectin from Enzo Life Science, Farmingdale N.Y.) in 600 µl of PBS supplemented with 0.1% BSA and 2 mM ethylenediaminetetracetic acid (pH 7.4) on ice for 30 minutes. After 30 minutes, the cells were washed once and incubated with 50 µl Dynabeads Biotin Binder (Invitrogen) at 4° C. with rotation for 30 minutes. A magnet was applied to deplete Dynabeads-bound α-Gal+ cells. The IB4 lectin is specific for the Gal epitope; cells that did not bind the Dynabeads remained in the supernatant. CMAH cells that did not bind IB4 and the Dynabeads were identified as Gal$^{-/-}$ cells. Crispr CMAH and GGTA1 treated cells that did not bind IB4 and the Dynabeads were utilized in SCNT as described below herein.

Example 6. TALEN Constructs

TALEN constructs are designed to bind and cleave the sequence of porcine CMAH at a suitable site. Additional Talen constructs are designed to bind and cleave GGTA1 at a suitable site.

Example 7. Production of Double Knockout (αGal and CMAH) Pigs

Somatic Cell Nuclear Transfer (SCNT) was performed using in vitro matured oocytes (DeSoto Biosciences Inc., St. Seymour Tenn. and Minitube of America, Mount Horeb, Wis.). Cumulus cells were removed from the oocytes by pipetting in 0.1% hyaluronidase. Oocytes with normal morphology and a visible polar body were selected and incubated in manipulation media (calcium-free NCSU-23 with 5% fetal bovine serum (FBS) containing 5 µg/ml bisbenzimide and 7.5 µg/mL cytochalasin B for 15 minutes. Following this incubation period, oocytes were enucleated by removing the first polar body and metaphase II plate. Single cells of CMAH deficient LDC that survived IB4 counterselection were injected into each enucleated oocyte. Alternatively Crispr transfected cells that survived IB4 counterselection were injected into each enucleated oocyte. Electrical fusion was induced with a BTX cell electroporator (Harvard Apparatus, Holliston, Mass.). Enucleated oocytes injected with a cell (couples) were exposed to two DC pulses of 140 V for 50 µs in 280 mM mannitol, 0.001 mM CaCl$_2$) and 0.05 mM MgCl$_2$. After one hour, reconstructed oocytes were activated by two DC pulses of 120 V for 60 µs in 280 mM mannitol, 0. 1 mM CaCl$_2$) and 0.05 mM MgCl$_2$. After activation, oocytes were placed in NCSU-23 medium with 0.4% bovine serum albumin (BSA) and incubated at 38.5° C., 5% CO$_2$ in a humidified atmosphere for less than one hour. Within an hour after activation, oocytes were transferred into a recipient pig. Recipient pigs were synchronized occidental pigs on their first day of estrus. Pregnancies were verified by ultrasound at day 25 or day 26 after embryo transfer. Results of SCNT using double knockout cells are summarized in Table 1. Results of SCNT using Crispr-transfected IB4 counterselected cells are summarized in Table 2.

TABLE 1

Results of somatic cell nuclear transfer using double-KO cells.

| Recipient | Donor cells | Embryos transferred | Pregnant | Stillborn | Live born | Cloning efficiency | Piglet birth weight (Avg) |
|---|---|---|---|---|---|---|---|
| 01 | LDC cl22 | 94 | Resorbed | — | — | — | — |
| 02 | LDC cl22 | 105 | Fetus collection day 30 | 1 | 5 | 5.7 | 0 |
| 03 | FF1* | 115 | No | | | | |
| 04 | FF1* | 121 | No | | | | |
| 05 | FF1* | 121 | Yes | 1 | 4 | 4.1 | 791 |
| 06 | FF1* | 120 | No | | | | |
| Total to term | 4 | 477 | ¼ (25%) | ⅕ (20%) | ⅘ (80%) | 0.8% | 791 |

Double-KO cells (cl22) were used as donor cells in SCNT and transferred into 2 recipients, 01 and 02. Fetal fibroblasts from fetus number 1 of recipient 02 were re-cloned and transferred to animals 03, 04, 05, and 06. 477 embryos were delivered to four gilts, resulting in one pregnancy and the birth of 5 piglets. The four viable piglets appeared healthy as they were nursing since birth and needed no feeding support.

In at least one experiment, SCNT of the selected cells deficient for CMAH and GGTA1 resulted in a pregnancy that was terminated at day 30 of gestation. Five normal fetuses and one resorbed fetus were harvested, photographed and shown in FIG. 1A. Red blood cells from the double knockout fetuses were analyzed by flow cytometry as described below herein.

Figures 3A, 3B:
FIG. 3A presents a photograph of viable double-KO piglets.
FIG. 3B provides sequence information regarding the wild-type (WT) sequences for the CMAH and GGTA1 target regions. The alterations that occur in the double-KO piglets in either the CMAH or GGTA1 target region are underlined, while the binding sites are italicized. SEQ ID NO:16 provides a portion of the wild-type CMAH gene sequence; SEQ ID NO:17 provides a disrupted version of the CMAH sequence. SEQ ID NO:18 provides a portion of the wild-type GGTA1 gene sequence; SEQ ID NO:19 provides a disrupted version of the GGTA1 gene sequence.

Fibroblasts were grown from fetus number one. The fibroblasts were utilized in SCNT to generate 477 embryos which were transferred into four recipient gilts. The SCNT resulted in one pregnancy and the birth of four live piglets and one stillborn piglet. The four viable piglets needed no feeding support and appeared healthy. Three of the αGal/CMAH double knockout pigs are shown in FIG. 3A. The above described disruptions of the CMAH and GGTA1 genes were validated in the four viable pigs from the second pregnancy as described below herein. Results of somatic cell nuclear transfer using double-KO cells are summarized in Table 1 above.

Crispr-transfected IB4 counterselected cells were used as donor cells in SCNT and transferred into 2 recipients, Juneau and Honda. Eighty-eight embryos were transferred into Juneau; pregnancy did not occur in Juneau. Over 100 embryos were transferred to Honda; pregnancy occurred. Ten healthy fetuses were collected at day 32 of gestation (FIG. 9A). DNA sequencing results showed that five out of the ten fetuses were GGTA1 and CMAH double knockouts.

For GGTA1, seven fetuses were biallelic mutations, one fetus was a monoallelic mutation and two fetuses were wild-type. For CMAH, five fetuses were biallelic mutations, one fetus was a monoallelic mutation and four fetuses were wild-type. Among the five double knockout fetuses, two homozygous mutations were found in fetus 7 at the GGTA1 locus and in fetus 2 at the CMAH locus. The remaining mutations were heterozygous biallelic mutations. Results are summarized in Table 2 below and sequence data are presented in FIG. 9B. Fetal fibroblasts were harvested from one double knockout fetus. The fetal fibroblasts were utilized in SCNT to generate embryos which were transferred into recipient sows. SCNT of the double knockout fetal fibroblasts resulted in at least one pregnancy.

Figure 2A:
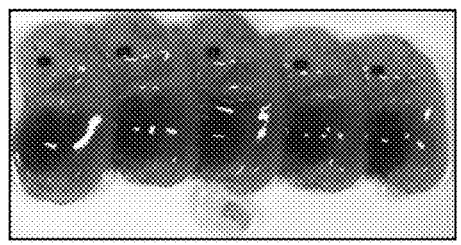
FIGS. 2A-2C provides genotype and phenotype analysis of double-KO fetuses.
Figure 2B:
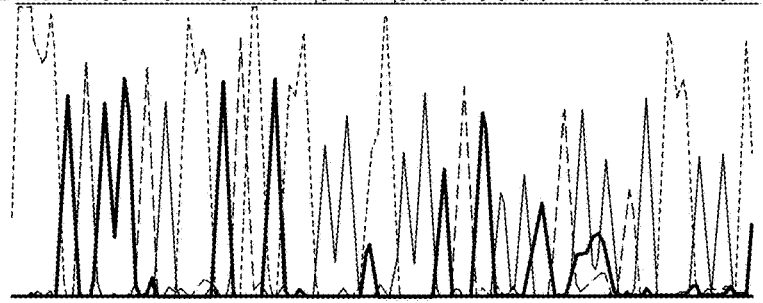

Results from an exemplary DNA sequence analysis are shown in FIG. 2B. DNA sequence analysis confirmed homozygous alterations of the GGTA1 and CMAH genes in at least one fetus. The CMAH gene sequence is altered by a four base pair insertion. The inserted sequence is "GGAA". The GGTA1 gene sequence is altered by a 3 base pair deletion adjacent to a G to A substitution. The sequences of the targeted CMAH and GGTA1 regions of the genomic DNA of four viable piglets are shown in FIG. 3B.

Genomic DNA from IB4 counter-selected cells and Crispr cloned fetuses was extracted using GenElute Mammalian Genomic DNA Miniprep Kit (Sigma Aldrich, St. Louis Mo.).

TABLE 2

Results of Somatic Cell Nuclear Transfer Using Crispr-Transfected Cells

| Recipient name | Donor cells | Transferred embryos | Pregnancy | Fetuses collected | dKO | Cloning efficiency** |
|---|---|---|---|---|---|---|
| Juneau | LDC | 88 | No | — | — | 0 |
| Honda | LDC | 103 | Yes | 10 | 5 | 9.7 |
| Total/Avg | | 191 | 50%* | 10 | 5 | 5.2 |

| | F1 | F2 | F3 | F4 | F5 | F6 | F7 | F8 | F9 | F10 |
|---|---|---|---|---|---|---|---|---|---|---|
| GGTA1 | KO (−/−) | KO (−/−) | KO (−/−) | HT (+/−) | KO (−/−) | KO (−/−) | KO (−/−) | KO (−/−) | WT (+/+) | WT (+/+) |
| CMAH | KO (−/−) | KO (−/−) | WT (+/+) | WT (+/+) | KO (−/−) | KO (−/−) | KO (−/−) | HT (+/−) | WT (+/+) | WT (+/+) |

Somatic Cell Nuclear Transfer. All the animals used in this study were approved by Institutional Biosafety Committee (IBC) and Institutional Animal Care and Use Committee (IACUC). In Table 2, * indicates pregnant animals/total recipients and ** indicates fetuses/embryos transferred.

Example 8. DNA Sequencing Analysis of Zn-Finger Targeted CMAH and GGTA1 Regions

Genomic DNA from double knockout Zn finger cloned fetuses and the four viable piglets was extracted using DNeasy Blood & Tissue Kit (Qiagen, Valencia, Calif.). PCR amplification of the CMAH region was performed as described above herein.

Primer CMAH-S 1 (SEQ ID NO: 5-5' CCAAACCCTGT-CATTCCAG 3') and GGTA1-F primer (SEQ ID NO: 6-5' CTAGAAATCCCAGAGGTTAC 3') were used to sequence the targeted CMAH region and GGTA1 region, respectively.

The GGTA1 region was amplified by PCR using the GGTA1-F primer (SEQ ID NO: 6 (5' CTAGAAATCCCAGAGGTTAC 3')) and GGTA1-R primer (SEQ ID NO:7 (5'TCCTTGTCCTGGAGGATTCC3')). Pwo Master (Roche, Indianapolis Ind.) was used and PCR conditions were as follows: 94° C., 2 min; 94° C., 15 s, 57° C., 30 s, and 72° C., 30 s for 40 cycles; and a final extension step of 72° C. for 5 min. A total of 200-400 ng of PCR product was denatured and annealed using the following program on a Mycycler (Bio-Rad): 95° C., 10 min; 95° to 85° C., −2° C./s; 85° C. to 25° C., −0.1° C./s. One microliter of enhancer and 1 μl of Nuclease S (Transgenomic Omaha Nebr.) was added to each reaction and incubated at 42° C. for 40 minutes. The product was separated on a 10% polyacrylamide gel and stained with SYBR Safe (Invitrogen USA Eugene Oreg.).

The GGTA1 region was amplified by PCR using the GGTA1-F seq primer (SEQ ID NO: 8 (5' CCT-TAGTATCCTTCCCAACCCAGAC-3')) and GGTA1-R seq primer (SEQ ID NO: 9 (5' GCTTTCTTTACGGTGTCAGT-GAATCC-3')). The CMAH region was amplified by PCR using the CMAH-F seq primer (SEQ ID NO: 10 (5'-CTTGGAGGTGATTTGAGTTGGG-3')) and the CMAH-R seq primer (SEQ ID NO: 11 (5'-CATTTTCTTCGGAGTT-GAGGGC-3')). Pwo Superyield DNA polymerase (Roche, Indianapolis Ind.) was used and PCR conditions for GGTA1 were as follows: 94° C., 2 min; 94° C., 15 s, 54° C., 30 s, and 72° C., 45s for 15 cycles; 94° C., 15 s, 54° C., 30 s, and 72° C., 45s+5 seconds/cycle for 25 cycles; and a final extension step of 72° C. for 5 min. The PCR conditions for CMAH were as follows: 94° C., 2 min; 94° C., 15 s, 56° C., 30 s, and 72° C., 45 s for 15 cycles; 94° C., 15 s, 56° C., 30 s, and 72° C., 45 s+5 seconds/cycle for 25 cycles; and a final extension step of 72° C. for 5 min. The products were separated on a 1% agarose gel, purified by the GenElute Gel Extraction kit (Sigma-Aldrich, St. Louis Mo.) and sequenced by the Sanger method (DNA Sequencing Core Facility, Indiana University School of Medicine).

Primer CMAH-F seq (SEQ ID NO: 10) and GGTA1-F seq primer (SEQ ID NO: 8) were used to sequence the targeted CMAH region and GGTA1 region, respectively.

Results from exemplary DNA sequence analyses are shown in FIG. 9B. DNA sequence analysis confirmed biallelic alterations of the GGTA1 and CMAH genes in five fetuses. In fetus 1 and 5, one GGTA1 allele has a single base pair deletion (deletes a C), the other allele has a single nucleotide insertion (T). In fetus 2, one GGTA1 allele has a six base pair deletion, the other allele has a two nucleotide insertion (AT). In fetus 6, one GGTA1 allele has a ten base pair deletion, the other allele has a seven base pair deletion. In fetus 7, both GGTA1 alleles have an eight nucleotide insertion that substitute for a five nucleotide sequence. In fetus 1, one CMAH allele has a double base pair deletion (deletes TG), the other allele has a single nucleotide insertion (inserts T). In fetus 2, both CMAH alleles have an 8 base pair deletion. In fetus 5, one CMAH allele has a 5 nucleotide deletion, the other has a 3 nucleotide deletion. In fetus 6, one CMAH allele has a single base pair deletion (T), the other has single base pair deletion and a colocalized two base pair insertion. In fetus 7, one CMAH allele has a 5 base pair deletion, the other has a 20 base pair deletion. Sequences of the targeted CMAH and GGTA1 regions of the genomic DNA of five fetuses are shown in FIG. 9B.

Example 9. Flow Cytometry of Red Blood Cells (RBCs)

Fetal livers were removed from double knockout fetuses and incubated in RPMI1640 for 24 hours at 37° C. RBCs were collected from cells released into the media after incubation of the fetal livers. RBC's were also obtained from adult human donors, six month old wild-type pigs and GGTA-knockout pigs (GGTA-KO pigs (fetal or 6 month old)). Porcine and human peripheral blood monocytes (PBMCs) were prepared using Ficoll-Paque Plus from whole blood collected in anticoagulant citrate dextrose (ACD).

Cells were stained with IB4 lectin Alexa Fluor 647 (Invitrogen, Grand Island, N.Y.) and anti-Neu5Gc antibody (Sialix, Vista Calif.). A negative control antibody for comparison with anti-Neu5Gc antibody was also used (Sialix, Vista Calif.). Cells were incubated with IB4 lectin for 20 minutes at 4° C. The cells were washed with blocking agent (Sialix, Vista, Ca) diluted in HBSS. Gal epitopes bind IB4 lectin. Cells were then stained with anti-Neu5Gc antibody for one hour at 4° C. followed by Donkey anti-chicken DyLight 649 (Jackson ImmunoResearch Laboratories Inc, West Grove Pa.) for 40-60 minutes at 4° C. Cells stained with anti-Neu5Gc antibody were washed before and after secondary antibody with Sialix blocking agent diluted in PBS. In various experiments unstained RBC or PBMC were used as negative controls for IB4 lectin staining. An Accuri C6 flow cytometer and CFlow Software (Accuri, Ann Arbor, Mich.) were used for analysis.

Figure 2C:
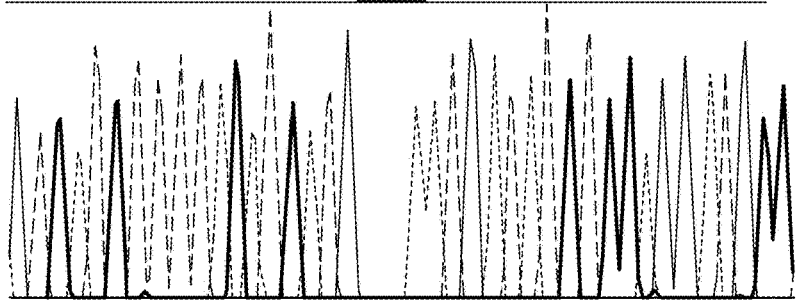

FACS analysis validated the absence of functional GGTA1 and CMAH genes eliminated the α-Gal and Neu5Gc modifications on the RBCs isolated from the cloned fetuses. Results obtained from one such experiment are shown in FIG. 2C.

Example 10. Confocal Microscopy Analysis

One of the four double knockout (Double-KO, DKO, CMAH-/αGAL-) piglets with mutations generated by Zn-finger targeting was euthanized. Liver, heart and kidney tissues were obtained from the double-ko pig. Liver, heart and kidney tissues were also obtained from wild-type (WT) and GGTA1 knockout (GGTA-ko) pigs. Frozen sections of each tissue were prepared. Mounted tissues were blocked in Odyssey blocking buffer (LI-Cor Biosciences, Lincoln Nebr.) in HBSS for one hour. The slides were then fixed in 4% paraformaldehyde for 10 minutes. Tissues were stained with IB4 lectin Alexa Fluor 647 (Invitrogen, Grand Island N.Y.) to visualize the presence of the Gal epitope. To visualize the Neu5Gc epitope, tissues were stained with a chicken anti-Neu5Gc antibody or with a control antibody (Sialix, Vista, Calif.) for one hour. Tissues were washed three times with HBSS. Donkey anti-chicken DyLight 649 (Jackson ImmunoResearch Laboratories Inc., West Grove Pa.) secondary antibody was incubated with the tissue for approximately one hour. Tissues were washed three times with 0.1% HBSS Tween. To stain the nucleus, DAPI stain (Invitrogen, Grand Island N.Y.) was added to all the slides for 1 minute followed by two 0.1% HBSS Tween washes. Tissues were mounted in ProLong Gold (Invitrogen, Grand Island N.Y.). Confocal microscopy was performed using an Olympus FV1000.

Figure 4A:
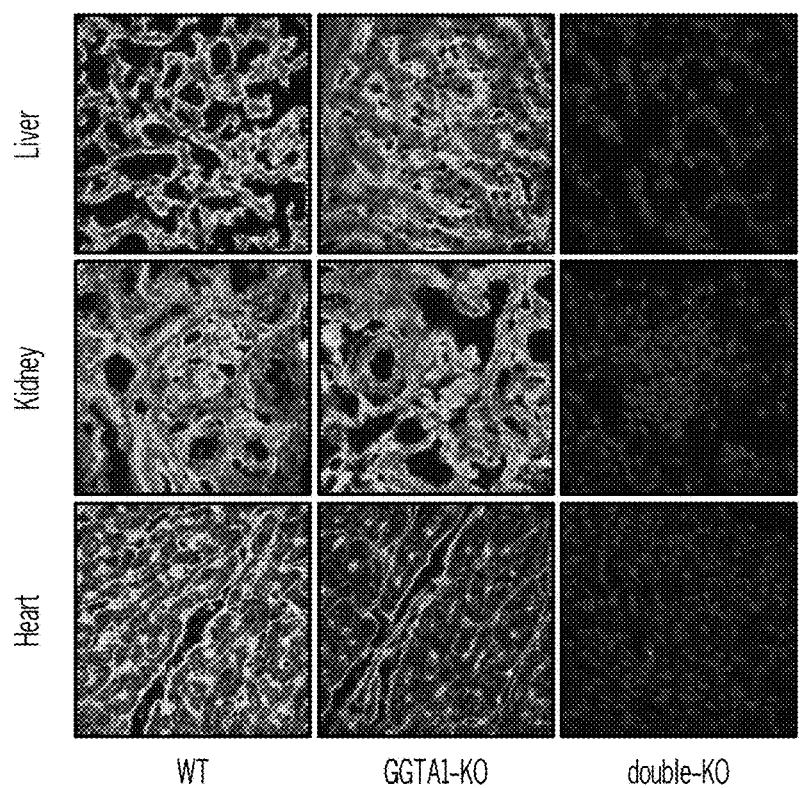
FIGS. 4A-4C present results from a series of experiments analyzing carbohydrate expression in genetically modified pigs.
Figure 4B:
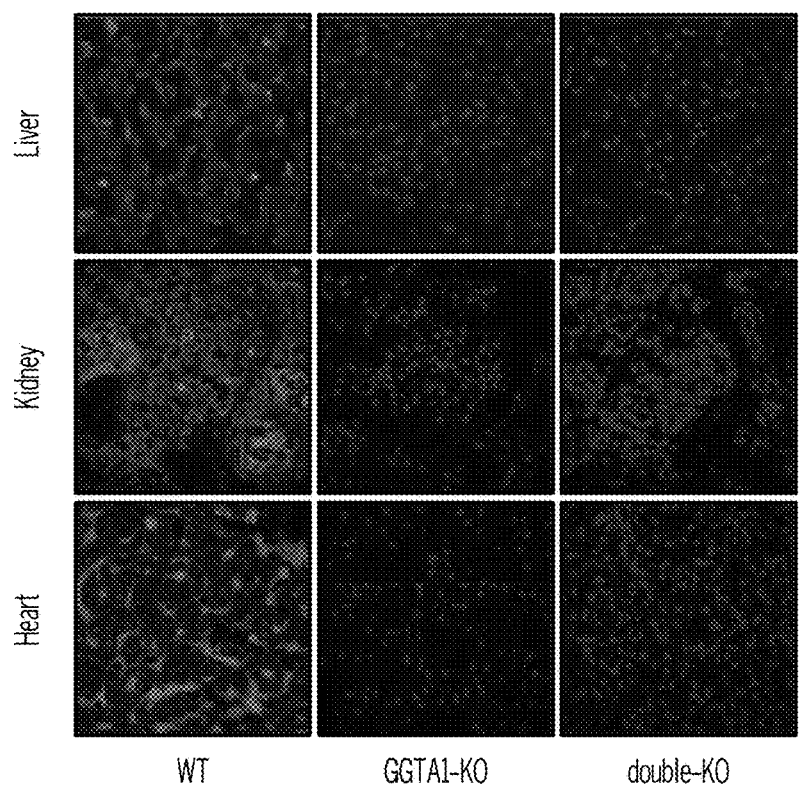
Figure 4C:
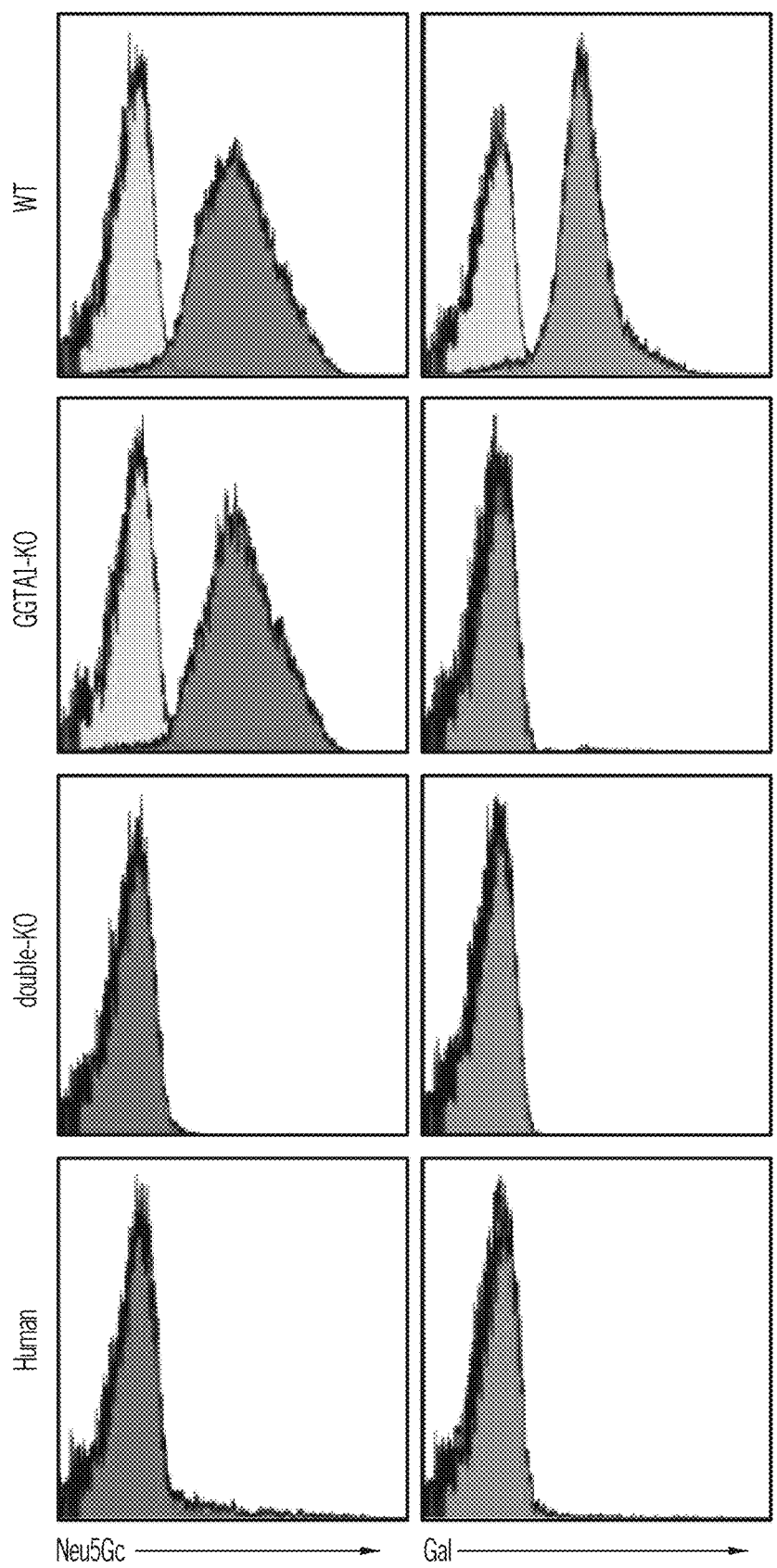

Confocal microscopy indicated the presence of α-Gal and Neu5Gc in liver, heart and kidney tissues obtained from a wild-type pig. GGTA1-KO pigs displayed only Neu5Gc in liver, heart and kidney tissues. Confocal microscopy indicated the absence of α-Gal and Neu5Gc in liver, heart and kidney in tissues obtained from a double knockout piglet (exemplary fields are shown in FIGS. 4A and 4B).

Example 11. Crossmatch of Human Sera with GGTA1-KO and Double-KO PBMCs

Figure 5A:
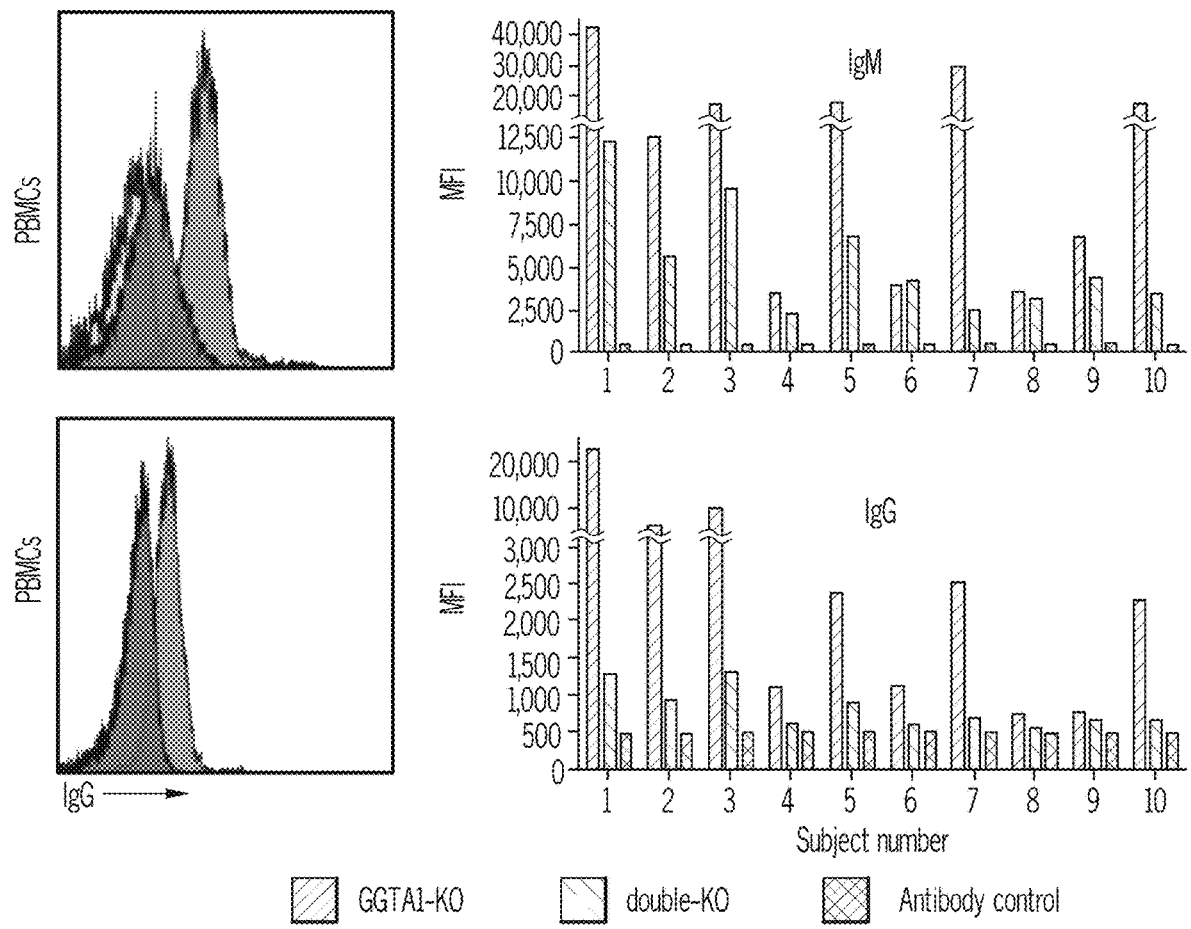
FIG. 5A and FIG. 5B presents results from a series of experiments examining human antibody recognition of PBMC from GGTA1-KO and double-KO pigs.

Porcine whole blood from GGTA1-KO and double-KO pigs was collected in ACD. Porcine PBMC's were prepared from the whole blood using Ficoll-Paque Plus. Cell viability was assessed microscopically with Trypan Blue. Sera were obtained from ten healthy human volunteers. Twenty-five percent heat-inactivated serum was prepared. Approximately $2\times10^6$/ml GGTA-KO and double-KO PBMCs were incubated with each human serum sample for 2 hours at 4° C. After incubation of the serum and PBMCs, the PBMCs were washed three times in 0.5% PBS Sialix Blocking agent. PBMCs were stained with DyLight 649-conjugated Donkey anti-human IgM or DyLight 488 Donkey anti-human IgG (Jackson Immunoresearch Laboratories Inc, West Grove Pa.) for 1 hour at 4° C. PBMCs were washed three times using 0.5% PBS Sialix blocking agent. Analyses were performed using an Accuri C6 flow cytometer and BD CFlow Plus Software (Accuri, Ann Arbor Mich.). Overlays were produced using Kaluza version 1.2 software from Beckman Coulter (Brea, Calif.). A representative histogram is shown in FIG. 5A. MFI's obtained from flow cytometry crossmatch analysis of 10 unique human subjects are also shown in FIG. 5A.

Lower Mean fluorescent Intensities (MFI) of double-KO PBMCs indicate less IgM bound to double-KO cells than to GGTA1-KO cells in 9 of 10 samples. In an experiment, the median MFI observed for human IgM binding to double-KO and GGTA-KO PBMCs were 4,411 and 15,059 respectively (n=10, p=0.0039). Lower MFI of double-KO PBMCs indicate less IgG bound to double-KO cells than to GGTA-KO cells in 10 of 10 samples. In an experiment, the median MFI observed for human IgG binding to double-KO and GGTA-KO PBMC were 714 and 2306 respectively (n=10, p=0.002). (FIG. 5A).

Example 12. Antibody-Mediated Complement-Dependent Cytotoxicity

Antibody-mediated complement dependent cytotoxicity assays are known in the art. A modified method of Diaz et al (Diaz et al, 2004, Transplant Immunology 13(4):313-317) was performed. Human serum was obtained from ten healthy volunteers (FIGS. 5 and 6). Twenty-five percent heat-inactivated human serum was prepared. The heat-inactivated human sera were serially diluted and 100 µl of each concentration were placed in a 96 well v-bottom assay plate. Sera were mixed with a 100 µl aliquot of PBMC obtained from either GGTA-KO or double-KO pigs. The final concentration of PBMC in each well was 5×10⁶/ml; in some experiments 1×10⁶/ml PBMC were used. The serum concentrations varied from 50%, 17%, 6%, 2%, 0.6%, 0.2% and 0.07%. The mixtures were incubated for 30 minutes at 4° C. After 30 minutes, the plates were centrifuged for 4 minutes at 400×g. The plates were decanted and washed with HBSS. Rabbit complement (150 µl of a 1:15 dilution) was added to each well and incubated for 30 minutes at 37° C. PBMC were labeled with a fluorescein diacetate (FDA) stock solution, prepared fresh daily in HBSS (1 µg/mL) from a 1 mg/ml stock solution in acetone and with propidium iodide (PI), prepared at 50 µg/ml in phosphate buffered saline (PBS). After incubation in complement, the samples were transferred by pipette to tubes containing 250 µl of HBSS and 10 µl of FDA/PI for analysis using an Accuri C6 flow cytometer.

The percentage of dead cells (PI+/FDA−), damaged cells (PI+/FDA+) and live cells (PI−/FDA+) was determined. Double negative events (PI−/FDA−) were excluded from calculations. The percentage of cytotoxicity in cells not exposed to serum was considered spontaneous killing (% $CTX_{spont}$). Values for cytotoxicity (% CTX) are shown after correction for spontaneous cytotoxicity (% $CTX_{spont}$), using the following formula: % CTX=(% $CTX_{exp}$−% $CTX_{spont}$)/(100−% $CTX_{spont}$)×100, where % $CTX_{exp}$ is the percentage of dead cells under the experimental condition.

Figure 5B:
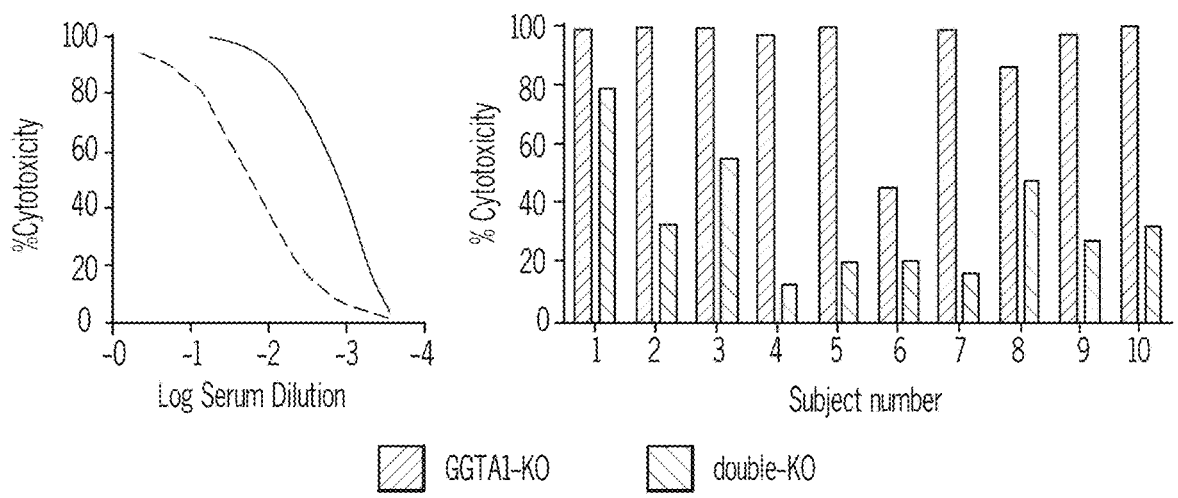
Figure 6:
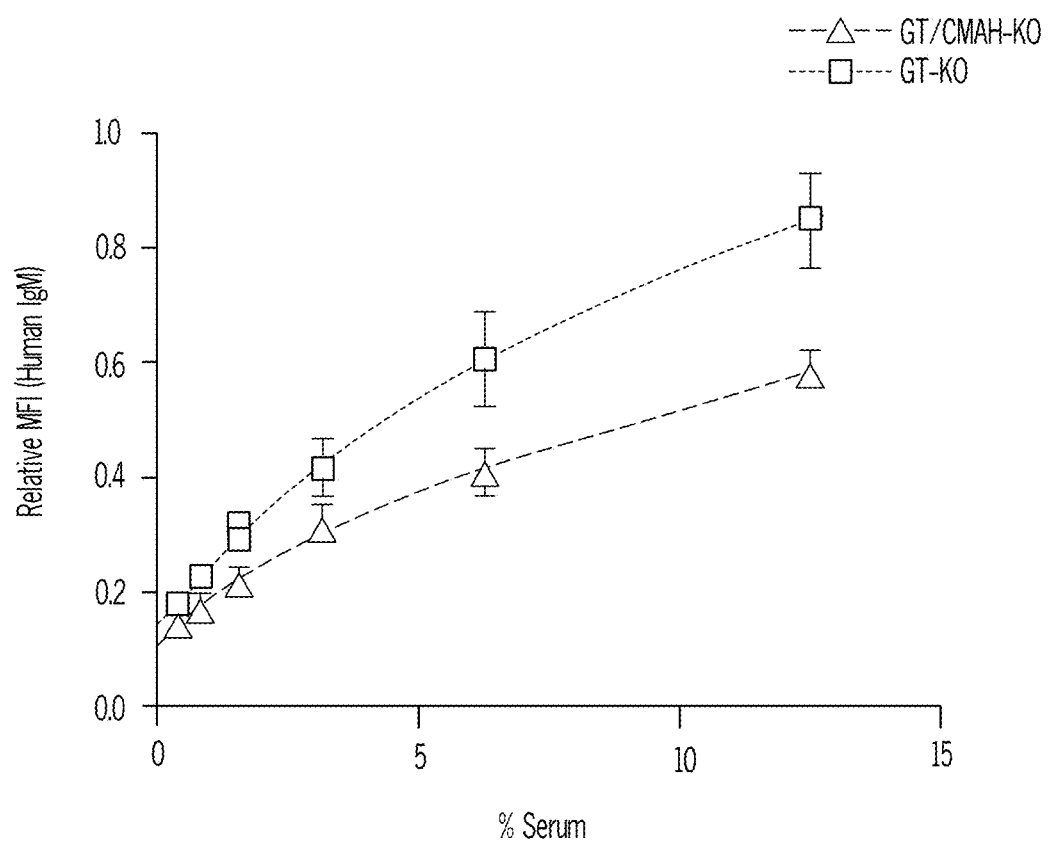
FIG. 6 shows flow cytometry used to analyze human antibody binding to GT-KO and GT/CMAH-KO porcine fetal fibroblasts in a dose dependent manner. GT/CMAH-KO cells bind less human IgM as compared to GT-KO porcine fetal fibroblasts.

Data from a series of antibody-mediated complement dependent cytotoxicity assays are shown in FIG. 5B. At 2% concentration, most of the subjects' sera lysed greater than 90% of GGTA1-KO PBMCs but less than 50% of the double-KO PBMCs. The median percent cytotoxicity of GGTA1-KO and double-KO PBMCs in this series was 98% and 29% respectively, at 2% human serum (n=10, p=0.002). The data shown indicate these human sera were less cytotoxic to double-KO cells than to GGTA1-KO cells. While not being bound by mechanism, the data suggest in the absence of the Gal epitope, a significant portion of IgM and IgG binding is to Neu5Gc.

Example 13. Statistical Analysis

Flow cytometric crossmatch results were reported as medians of the MFI values for each human serum crossmatched with GGTA1-KO and double-KO PBMCs for both IgM and IgG. The Wilcoxon matched pairs signed rank test was used to analyze the data using Prism 5 for Windows (GraphPad Software Inc, La Jolla Ca).

Antibody-mediated, complement dependent cytotoxicity data was also analyzed as above. The log of each serum dilution was plotted against the % CTX for each sample and the sigmoid curve was analyzed by non-linear regression to estimate the serum LD50. The % CTX of GGTA1-KO and double-KO PBMCs at each serum dilution for each sample was analyzed using the Wilcoxon matched pairs signed rank test.

Example 14. Ex Vivo Perfusion of Human Platelet Through a Double KO Liver

A double knockout CMAH/αGal pig is anesthetized and intubated. A midline abdominal incision is made. The liver is removed and placed in a perfusion device under normothermic conditions. Humidity, temperature and air flow are maintained in the perfusion device. Human platelets obtained from healthy volunteer subjects are circulated through the double knockout liver. Platelet levels in the pre-perfusion and post-perfusion samples are evaluated. Pre and post-perfusion evaluation of the pig liver is performed.

Example 15. Evaluation of Response to a Double Knockout (αGal and CMAH) Xenograft A porcine liver obtained from double knockout (αGal-/CMAH-) pigs is surgically transplanted into a recently deceased human cadaver using the piggyback method. After the surgery, biological samples are obtained from the human cadaver. Clinical indicia of graft rejection are monitored.

Example 16. Evaluation of a Response to a Double Knockout (αGal and CMAH) Xenograft Porcine kidneys are obtained from double knockout (GGTA1/CMAH double-KO) pigs. A highly sensitized human subject is administered compounds to manage pre-existing and de novo donor-specific antibodies. Porcine double-KO kidneys are surgically transplanted into the subject. Clinical indicia of graft rejection are monitored.

Example 17. Construction of Single Guide RNAs (s2RNAs) Expression Vector

Targeting sites for the CMAH and GGTA1 genes were identified. Forward and reverse oligonucleotides for each targeting site were obtained. The GGTA1 forward sgRNA sequence was CACCGAGAAAATAATGAATGTCAA (SEQ ID NO: 12); the GGTA1 reverse sgRNA sequence was AAACTTGACATTCATTATTTTCTC (SEQ ID NO: 13). The CMAH forward sgRNA sequence was CACCGAGTAAGGTACGTGATCTGT (SEQ ID NO: 14); the CMAH reverse sgRNA sequence was AAACACAGATCACGTACCTTACT (SEQ ID NO: 15). The oligonucleotide pairs were annealed together to generate short double strand DNA fragments with Bbs1 compatible overhangs. The pX330 bicistronic expression vector expressing Cas9 and sgRNA of interest (Addgene, www.addgene.org/crispr-cas) was linearized with Bbs1. pX330 expresses a mammalian codon optimized Cas9. The linearized pX330 expression vector and the double strand DNA fragments for each sgRNA (GGTA1 and CMAH) were incubated with ligase.

Liver derived cells (LDCs) were cultured as described in Li et al (2013) *J. Surg Res* 181:e39-45, herein incorporated by reference in its entirety. LDC were cotransfected with pX330-CMAHsgRNA and pX300-GGTA1sgRNA expression plasmids using the Neon transfection system (Invitrogen) according to the manufacturer's instructions. Forty-eight hours after transfection, cells were harvested and used for isolectin B4 counter-selection.

Example 18. Flow Cytometry Analysis

Figure 7A:
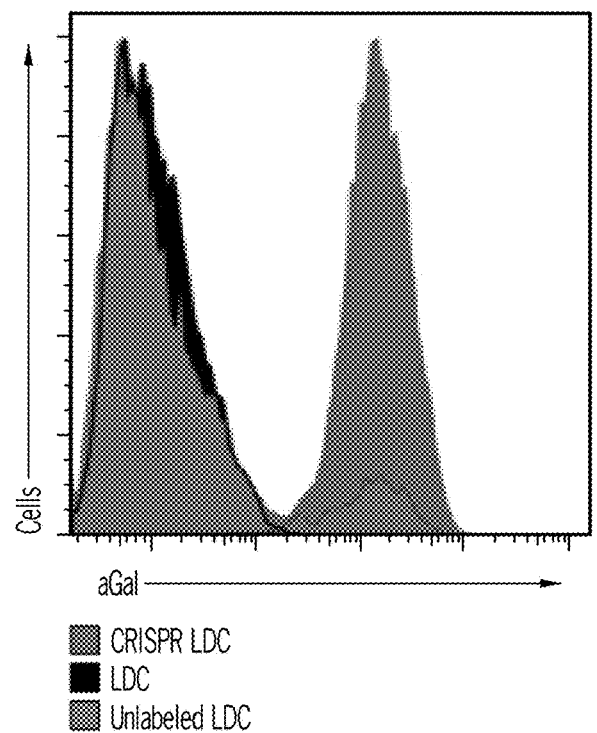
FIG. 7A and FIG. 7B provides panels pertaining to the generation of GGTA1/CMAH double knockout porcine LDCs through a CRISPR/Cas9 technique. LDCs that survived IB4 lectin counter-selection were expanded and stained with 1B4-FITC.
Figure 7B:
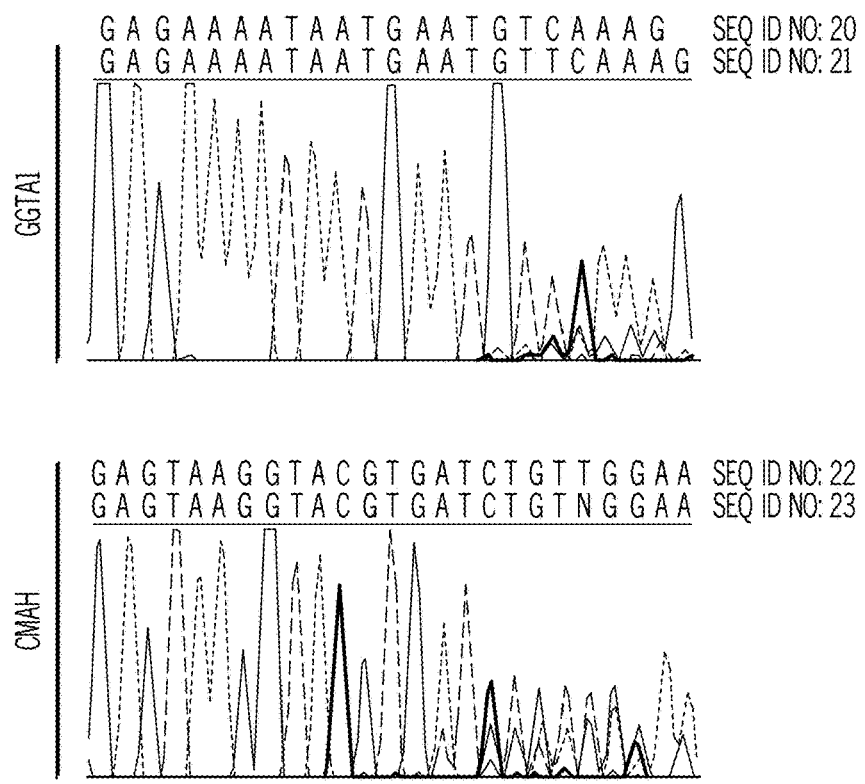
Figure 8A:
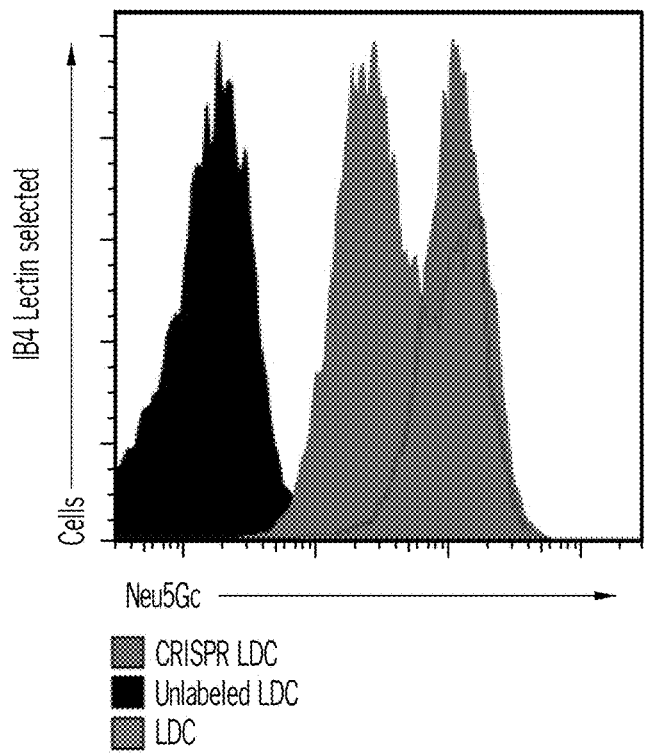
FIG. 8A and FIG. 8B depicts flow cytometry results of labeled liver derived cells (LDCs) simultaneously transfected with CrispR CMAH and α-Gal targeting plasmids (CRISPR LDC); labeled, non-transfected LDC; and unlabeled LDC. CMAH expression in the cells was evaluated by assessing the anti-Neu5Gc antibody binding to Neu5Gc epitopes on the cell surface. CMAH produces Neu5Gc. As shown in Panel B (Unselected) a small percentage of the bulk transfected cell population shows a CMAH deficiency. As shown in Panel A, after IB4 lectin counter-selection of the bulk cell population, a significantly higher percentage of the IB4 nonbinding cells (IB4 lectin selected) were CMAH deficient cells. In one experiment, 41.6% of the IB4 counter-selected cells were CMAH deficient while 6.7% of unselected bulk transfected cells were CMAH deficient.
Figure 8B:
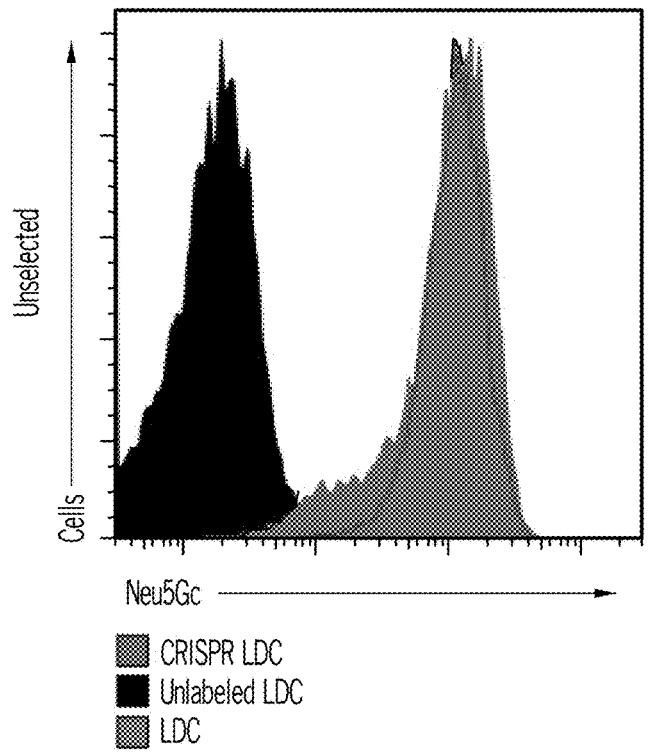
Figure 9C:
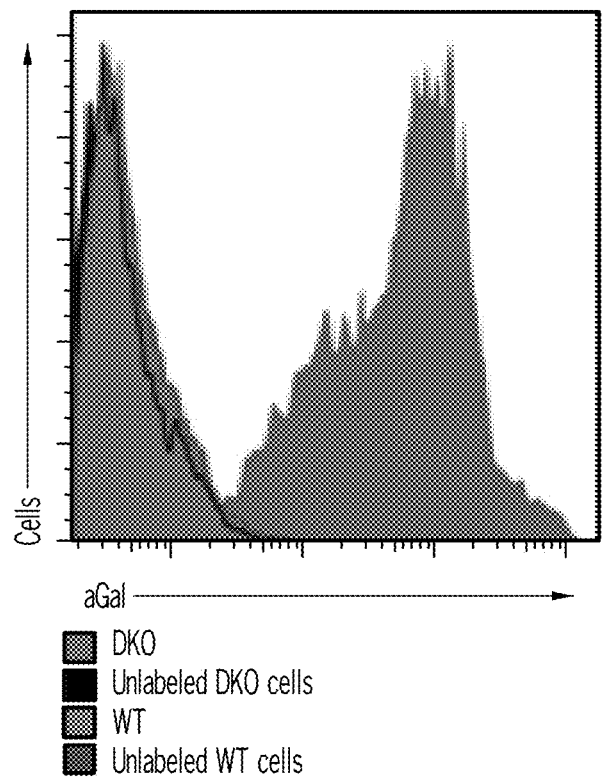
Figure 9C:
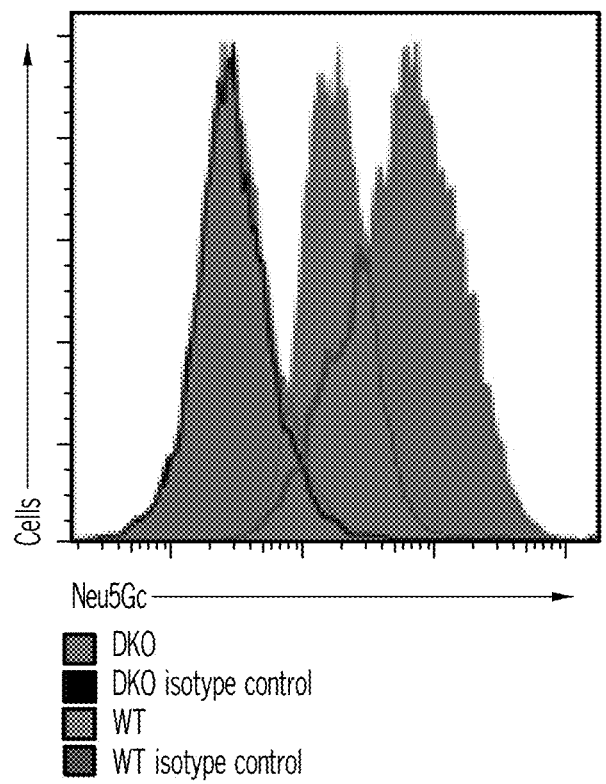

Isolectin B4 (IB4) counter-selected LDC, cloned fetal fibroblasts from DKO fetuses, wild-type LDC and wild-type fetal fibroblasts were stained with IB4 conjugated with FITC (Enzo Life Science, Farmingdale N.Y.) to assess the αGal epitope level. To evaluate the Neu5Gc level, IB4 counter-selected LDC cloned fetal fibroblasts from DKO fetuses, wild-type LDC and wild-type fetal fibroblasts were stained with antiNeu5Gc antibody (Sialix, Vista Calif.) followed by donkey anti-chicken DyLight 649 (Jackson ImmunoResearch Laboratories Inc., West Grove Pa.). A negative control antibody for comparison with anti-Neu5Gc antibody was also used (Sialix, Vista Calif.). An Accuri C6 flow cytometer (Accuri, Ann Arbor Mich.) and FlowJo software (Tree Star, Inc. Ashland Oreg.) were used for analysis. Representative flow cytometry results of αGal from IB4 counter selected cells are shown in FIG. 7A. Representative flow cytometry results of Neu5Gc on IB4 counter selected cells are shown in FIG. 8A. Representative flow cytometry results of the αGal and Neu5Gc on fetal fibroblasts derived from fetus 7 are shown in FIG. 9C.

Example 19. Ex Vivo Perfusion of Human Platelets Through a Double KO Liver

Figure 12:
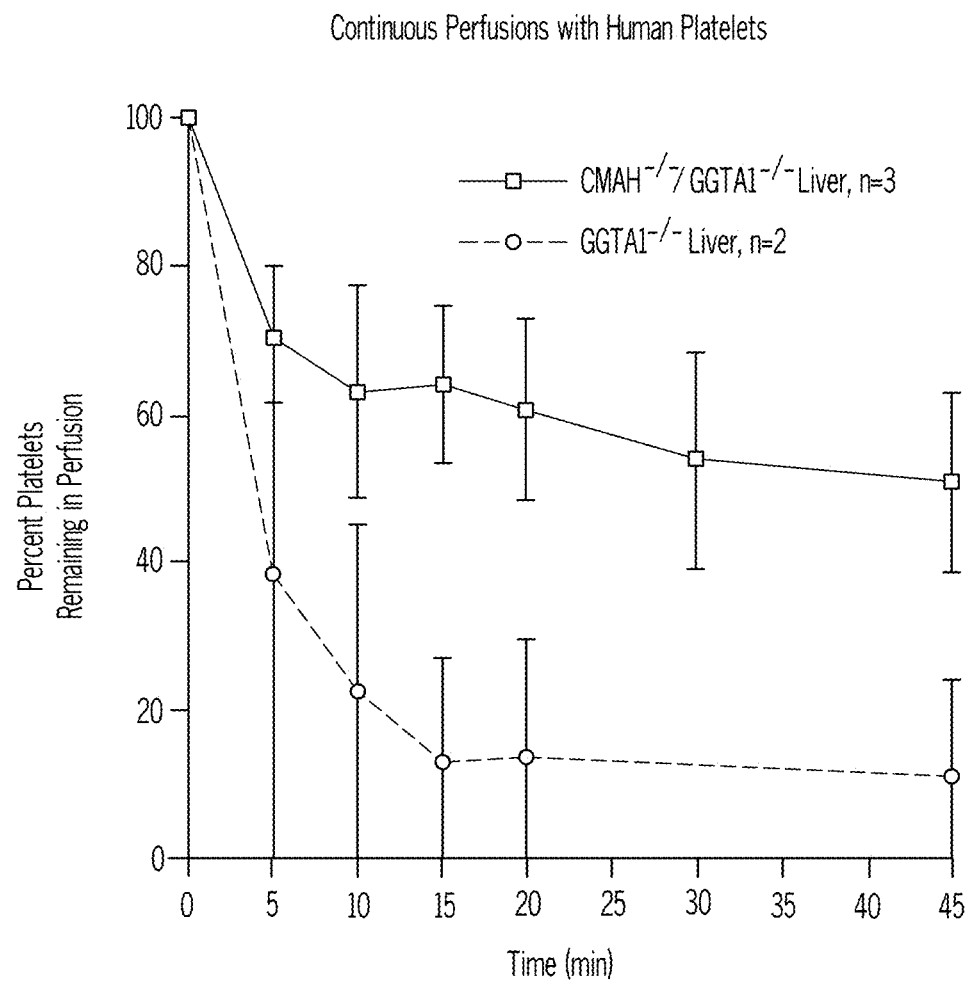
FIG. 12 provides a graph of data obtained from perfusion experiments involving porcine livers perfused with human platelets. The post-perfusion initiation time in minutes is indicated on the x-axis (Time); the percent of human platelets remaining in the perfusion solution is indicated on the y-axis (Percent Platelets Remaining in Perfusion). Data obtained from experiments with single αGal knockout pig livers (GGTA1$^{-/-}$, n=2) and CMAH/αGal DKO livers (CMAH$^{-/-}$/GGTA$^{-/-}$, n=3) are provided.

Double knockout CMAH/αGAL and single αGal knockout pigs were anesthetized and intubated. A midline abdominal incision was made in each pig. Livers were removed and placed in a perfusion device under normothermic conditions. Humidity, temperature and air flow were maintained in the perfusion device. Human platelets obtained from healthy volunteer subjects were circulated through the double knockout liver. Platelet levels in the pre-perfusion and post-perfusion samples were evaluated after circulation through three double knockout (CMAH$^{-/-}$/GGTA1$^{-/-}$) livers. Pre and post-perfusion evaluation of the pig livers were performed. GGTA1$^{-/-}$ livers (n=2) were obtained, and the livers were perfused under similar conditions. Data from one experimental series are summarized in FIG. 12.

Figure 10A:
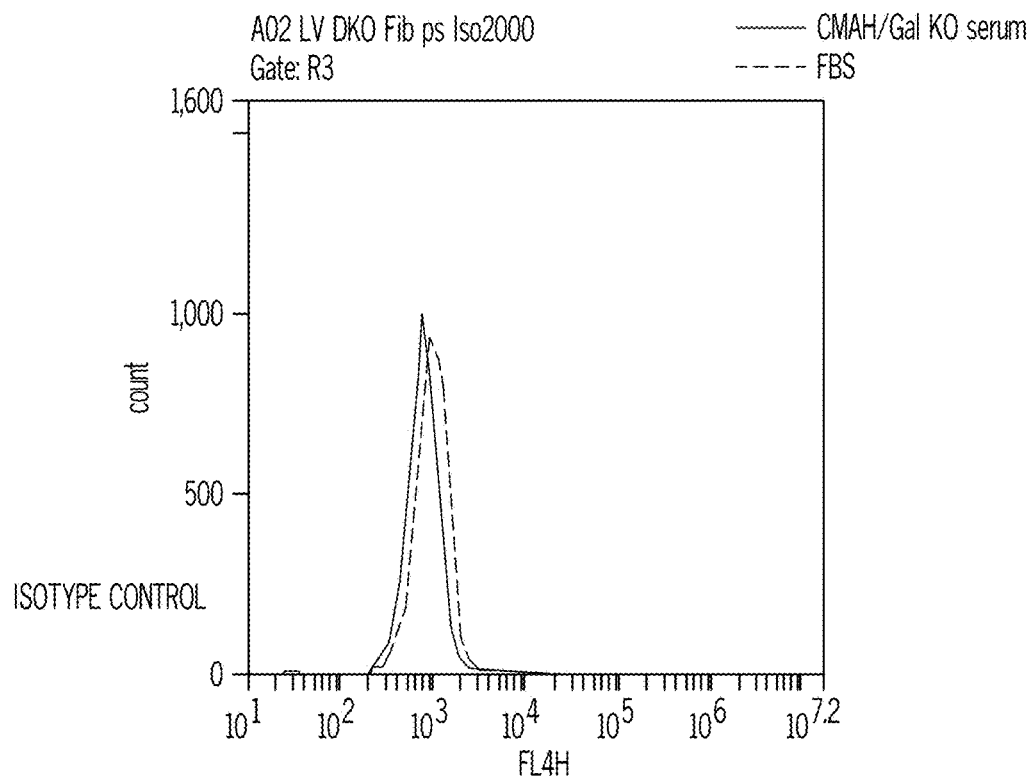
FIG. 10A and FIG. 10B provides panels of flow cytometry analysis of Neu5Gc on CMAH/GAL double knockout fibroblast cells grown in media supplemented with either fetal bovine serum (FBS) or CMAH/αGAL double knockout derived serum (CMAH/Gal KO).
Figure 10B:
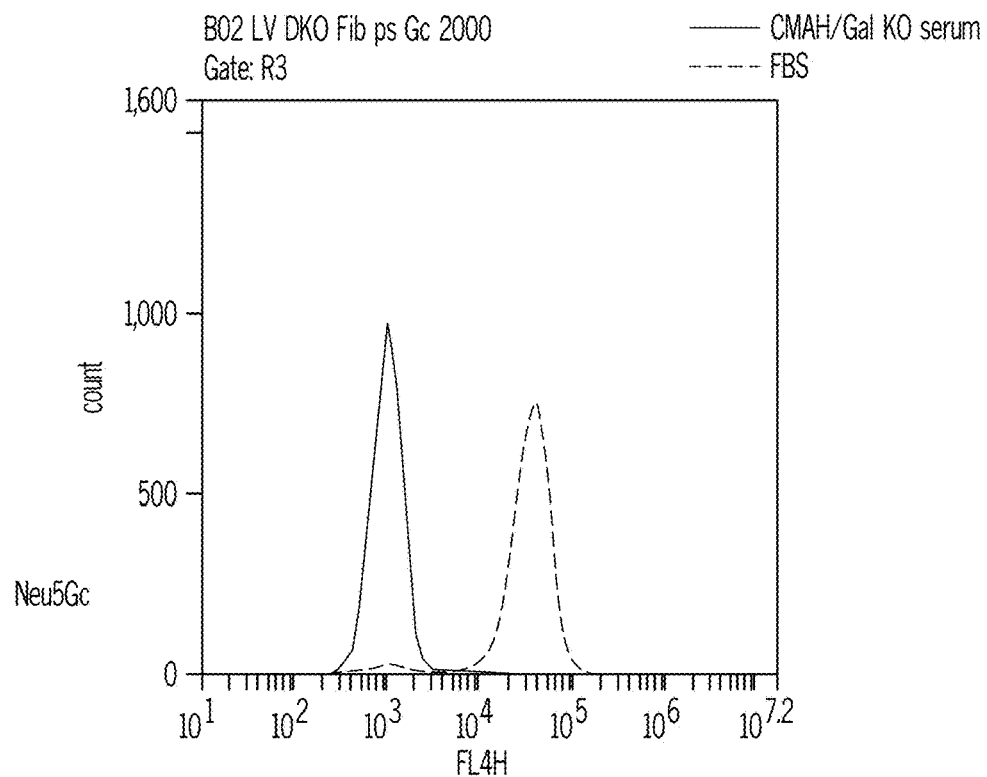
Figure 11A:
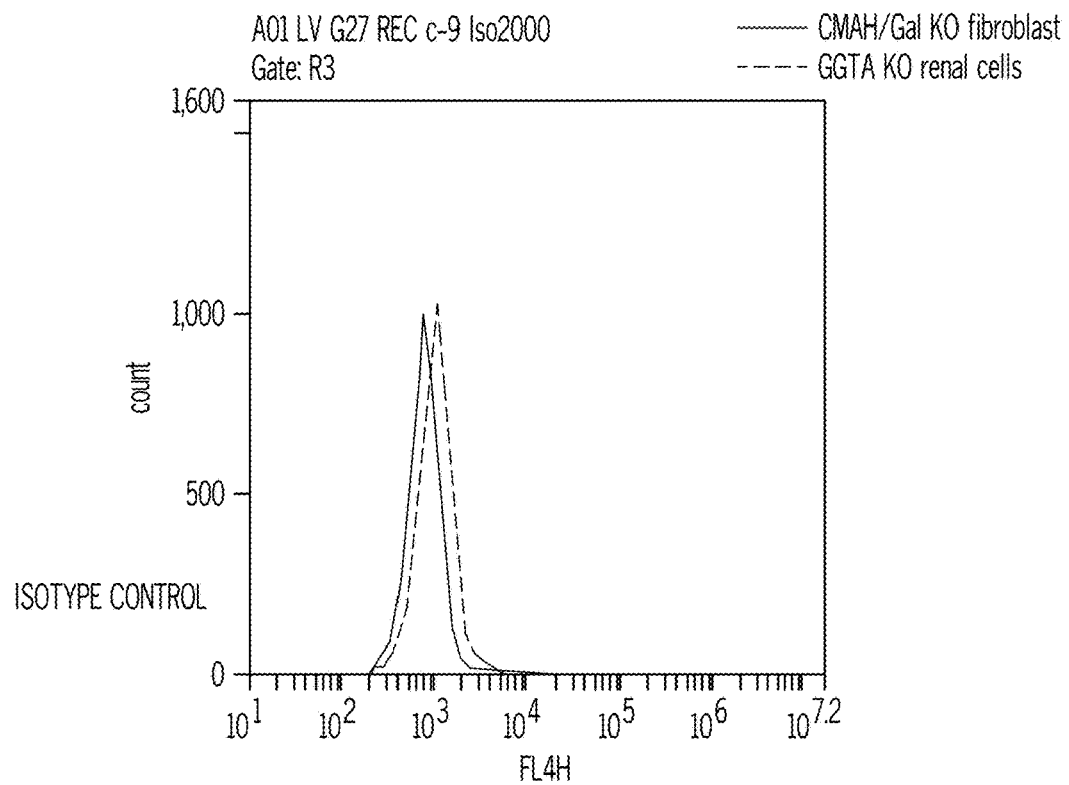
FIGS. 11A-11B provides panels of flow cytometry analysis of Neu5Gc on double knockout (CMAH/Gal KO) fibroblasts and single αGal knockout (GGTA KO) renal cells grown with a variety of cell culture reagents.
Figure 11B:
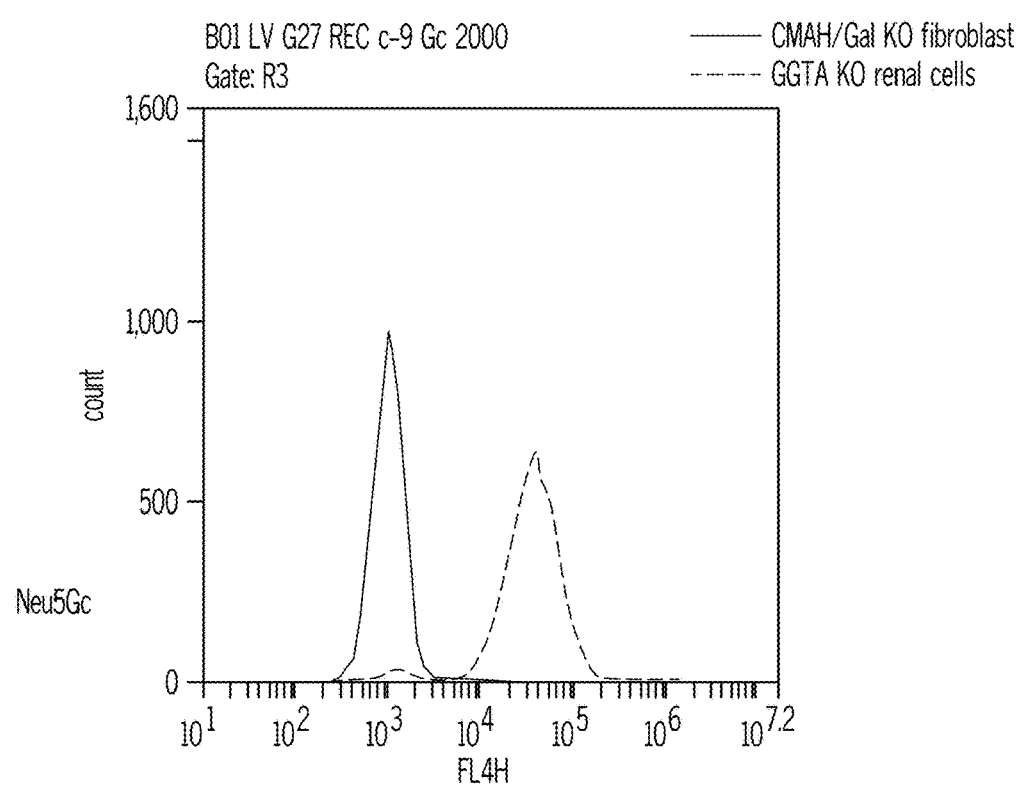

Example 20. Neu5Gc Levels in Cells Cultured with a DKO (αGal/CMAH) Pig Cell Culture Reagent Fibroblasts were cultured from a CMAH/αGal Double knockout pig. Because the DKO fibroblasts lack CMAH, they do not produce Neu5Gc. DKO serum was isolated from the blood of CMAH/αGAL pigs. The DKO fibroblasts were cultured in cell culture media supplemented with either DKO serum or bovine serum (FBS) for six weeks. After six weeks, cells were evaluated by flow cytometry with anti-Neu5Gc antibodies. Results from one such experiment are presented in FIG. 10.

Example 21. Concordant Analysis of DKO Pig, Baboon and Chimpanzee Material

Antibody-mediated complement dependent cytotoxicity assays are known in the art. A modified method of Diaz et al (Diaz et al, 2004, Transplant Immunology 13(4):313-317) was performed. Serum samples were obtained from 10 randomly selected baboons. Twenty-five percent heat-inactivated baboon serum was prepared. The heat-inactivated baboon sera were serially diluted and 100 µl of each concentration were placed in a 96 well v-bottom assay plate. Sera were mixed with a 100 µl aliquot of PBMC obtained from either GGTA1-KO or double-KO (GGTA1/CMAH DKO) pigs. The final concentration of PBMC in each well was $5\times10^6$/ml; in some experiments $1\times1010^6$/ml PBMC were used.

The mixtures were incubated for 30 minutes at 4° C. After 30 minutes, the plates were centrifuged for 4 minutes at 400×g. The plates were decanted and washed with HBSS. Rabbit complement (150 µl of a 1:15 dilution) was added to each well and incubated for 30 minutes at 37° C. PBMC were labeled with a fluorescein diacetate (FDA) stock solution, prepared fresh daily in HBSS (1 µg/mL) from a 1 mg/ml stock solution in acetone and with propidium iodide (PI), prepared at 50 µg/ml in phosphate buffered saline (PBS). After incubation in complement, the samples were transferred by pipette to tubes containing 250 µl of HBSS and 10 µl of FDA/PI for analysis using an Accuri C6 flow cytometer.

Figure 13:
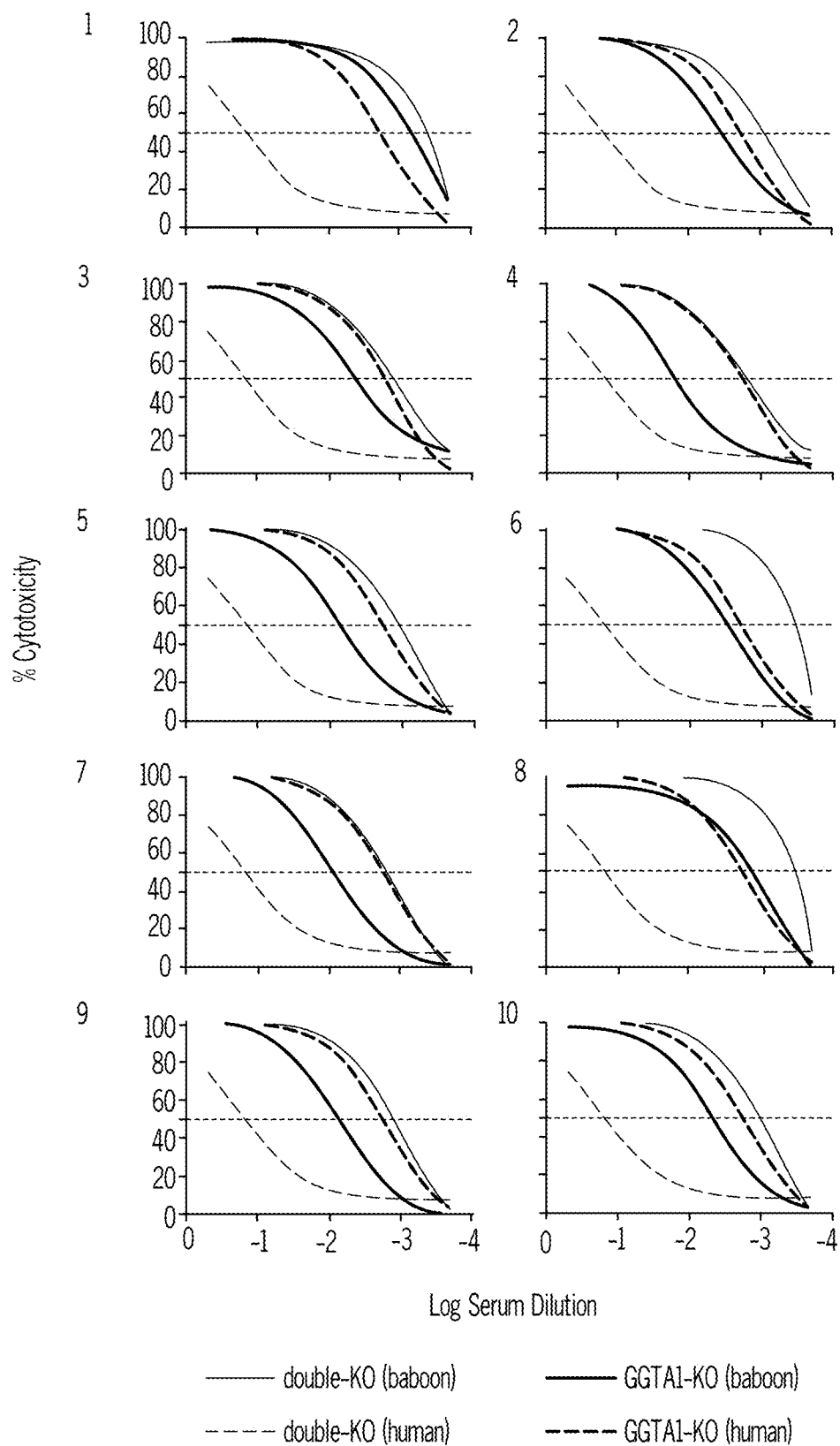
FIG. 13 provides individual curves for antibody-mediated, complement-dependent cytotoxicity of 10 randomly selected baboon serum samples against single (GGTA1-KO) and GGTA1/CMAH double (double-KO) peripheral blood monocytes (PBMCs). Results from a human serum sample against single (GGTA1-KO) and double-KO PBMC are also shown on each graph. Unexpectedly cytotoxicity of the baboon serum to the CMAH/αGAL double knockout PBMC differed widely from cytotoxicity of human serum to CMAH/αGal PBMCs. Cytotoxicity of baboon serum with CMAH/αGal double knockout PBMCs consistently increased as compared to cytotoxicity of baboon serum with αGal single knockout PBMCs. The dashed horizontal line indicates 50% killing. The % CTX for each sample was plotted against the log of each serum dilution and the sigmoid curve was analyzed by non-linear regression.

The % CTX for each sample was plotted against the log of each serum dilution and the sigmoid curve was analyzed by non-linear regression. Data from one such set of experiments are presented in FIG. 13.

Figure 14A:
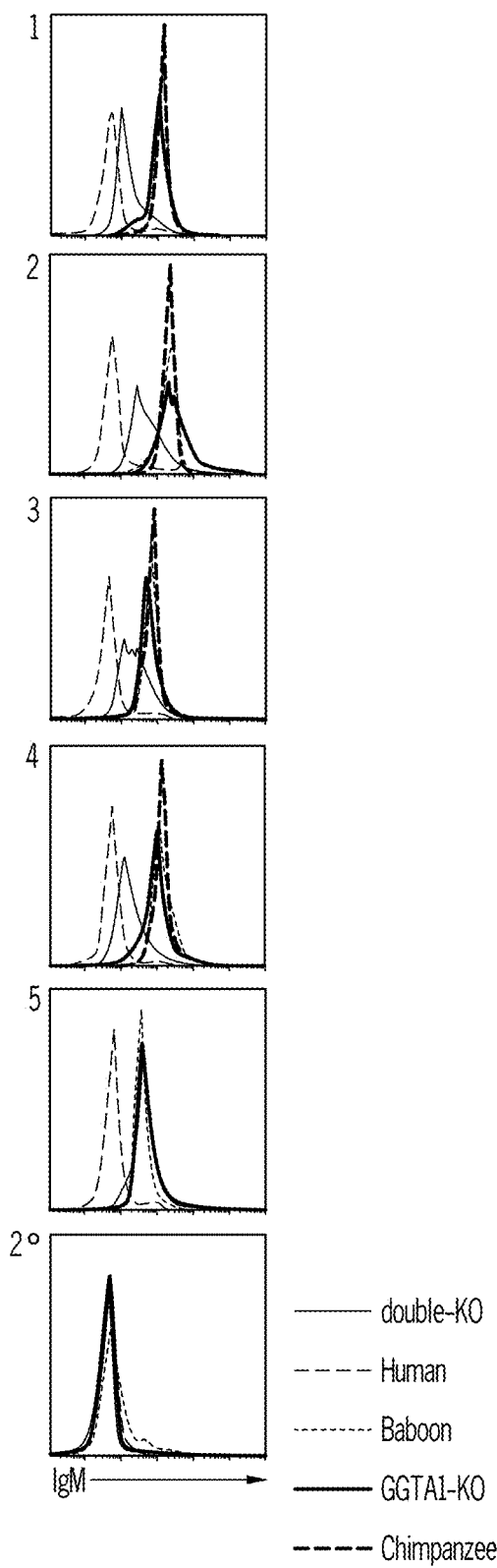
FIG. 14A and FIG. 14B provide histograms showing results of flow cytometry analysis of IgM (FIG. 14A) and IgG (FIG. 14B) antibody recognition. Histograms show the results of 5 randomly selected human sera (1, 2, 3, 4 and 5) incubated with GGTA1-KO pig, double-KO pig, baboon, chimpanzee and human PBMCs. Secondary only control antibody staining is shown in the bottom graph in each column. In four of the five samples shown, IgG antibody recognition for CMAH/GAL DKO PBMC and human PBMC yield almost overlaying traces. In the same four samples shown, the IgM traces for the CMAH/GAL DKO PBMC are shifted closer to the traces for the human PBMC than the baboon, chimpanzee and single knockout (GGTA1-KO) traces.
Figure 14B:
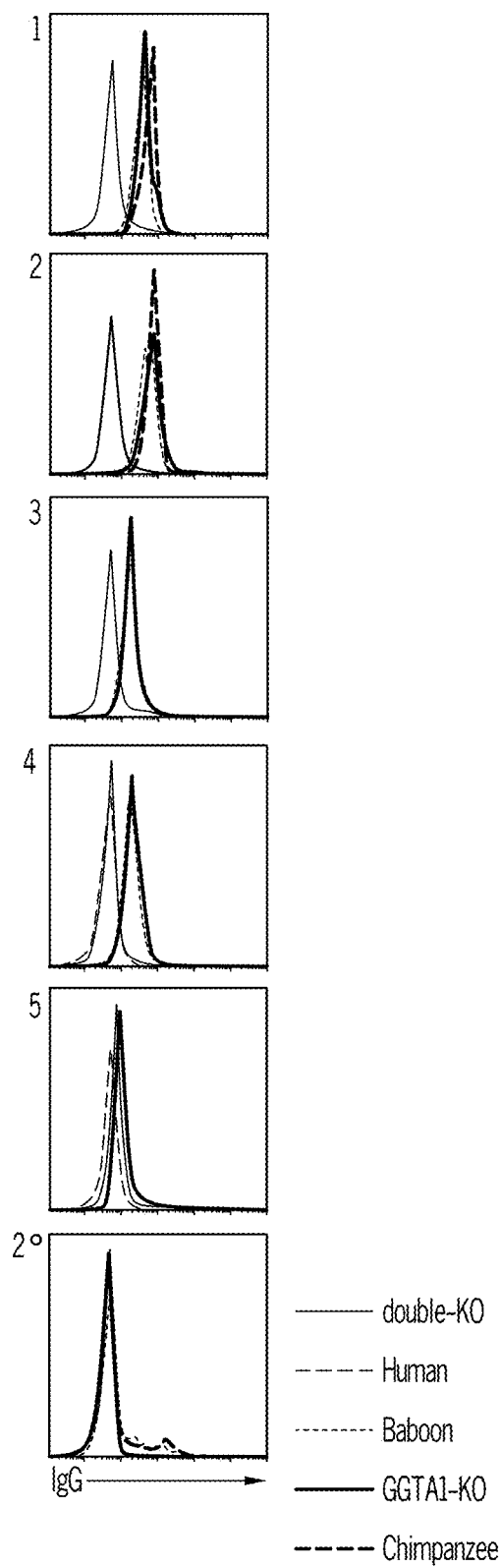

Serum was obtained from five randomly selected human donors. Twenty-five percent heat-inactivated serum was prepared. Human, baboon and chimpanzee PBMCs were obtained. PBMCs were obtained from single αGal knockout pigs (GGTA1-KO) and double CMAH/αGal (double-KO) pigs. Approximately $2\times10^6$/ml PBMCs were incubated with each human serum sample for 2 hours at 4° C. After incubation of the serum and PBMCs, the PBMCs were washed three times in 0.5% PBS Sialix Blocking agent. PBMCs were stained with DyLight 649-conjugated Donkey anti-human IgM or DyLight 488 Donkey anti-human IgG (Jackson Immunoresearch Laboratories Inc, West Grove Pa.) for 1 hour at 4° C. PBMCs were washed three times using 0.5% PBS Sialix blocking agent. Analyses were performed using an Accuri C6 flow cytometer and BD CFlow Plus Software (Accuri, Ann Arbor Mich.). Overlays were produced using Kaluza version 1.2 software from Beckman Coulter (Brea, Calif.). Secondary only control antibody staining was also evaluated. Histograms from one such experiment are presented in FIG. 14.

The invention is not limited to the embodiments set forth herein for illustration, but includes everything that is within the scope of the claims. Furthermore, all references cited herein are hereby incorporated by reference in their entirety and for all purposes as if fully set forth herein.

---

The invention claimed is:

1. A method of increasing the duration of the period between when a human subject is identified as a subject that would benefit from a human liver transplant and when said human liver transplant occurs, said method comprising providing a liver or liver tissue from a pig comprising α(1,3)-galactosyltransferase (αGal) and cytidine monophosphate-N-acetylneuraminic acid hydroxylase (CMAH) genes disrupted via gene editing, wherein expression of functional αGal gene product and CMAH gene product in said pig is decreased as compared to a wild-type pig, and surgically attaching said liver or liver tissue from said pig to a human subject in a therapeutically effective manner.

2. The method of claim 1, wherein said liver or liver tissue from said pig is internal to said human subject when surgically attached.

3. The method of claim 1, wherein said liver or liver tissue from said pig is external to said human subject when surgically attached.

4. The method of claim 1, wherein the gene editing is zinc finger gene editing.

5. The method of claim 1, wherein the gene editing is TALEN gene editing.

6. The method of claim 1, wherein the gene editing is CRISPR gene editing.

7. The method of claim 1, wherein the disruption of said αGal gene is selected from the group consisting of a 3 base pair deletion adjacent to a G to A substitution, a single base pair deletion, a single base pair insertion, a six base pair deletion, a two base pair insertion, a ten base pair deletion, a seven base pair deletion, and an eight base pair substitution for a five base pair sequence and wherein expression of functional αGal in said pig is decreased as compared to a wild-type pig.

8. The method of claim 7, wherein the disruption of said CMAH gene is selected from the group consisting of a four base pair insertion, a two base pair deletion, a single base pair deletion, a single base pair insertion, an eight base pair deletion, a five base pair deletion, a three base pair deletion, a two base pair substitution for a single base pair, and a twenty base pair deletion; and wherein expression of functional CMAH in said pig is decreased as compared to a wild-type pig.

9. The method of claim 1, wherein the disruption of said CMAH gene is selected from the group consisting of a four base pair insertion, a two base pair deletion, a single base pair deletion, a single base pair insertion, an eight base pair deletion, a five base pair deletion, a three base pair deletion, a two base pair substitution for a single base pair, and a twenty base pair deletion; and wherein expression of functional CMAH in said pig is decreased as compared to a wild-type pig.

10. A method of improving a hyperacute rejection related symptom in a human subject comprising transplanting a porcine organ, tissue or cells having reduced expression of α(1,3)-galactosyltransferase (αGal) and cytidine monophosphate-N-acetylneuraminic acid hydroxylase (CMAH) into the human subject, wherein said reduced expression is by virtue of disruption of the αGal and CMAH genes via gene editing in said porcine organ, tissue or cells and wherein said hyperacute rejection related symptom is improved as compared to when a porcine organ, tissue, or cells from a wild-type pig is transplanted into a human subject.

11. The method of claim 10, wherein the gene editing is zinc finger nuclease gene editing.

12. The method of claim 10, wherein the gene editing is TALEN gene editing.

13. The method of claim 10, wherein the gene editing is CRISPR gene editing.

14. The method of claim 10, wherein the disruption of said αGal gene is selected from the group consisting of a 3 base pair deletion adjacent to a G to A substitution, a single base pair deletion, a single base pair insertion, a six base pair deletion, a two base pair insertion, a ten base pair deletion, a seven base pair deletion, and an eight base pair substitution for a five base pair sequence and wherein expression of functional αGal in said pig is decreased as compared to a wild-type pig.

15. The method of claim 14, wherein the disruption of said CMAH gene is selected from the group consisting of a four base pair insertion, a two base pair deletion, a single base pair deletion, a single base pair insertion, an eight base pair deletion, a five base pair deletion, a three base pair deletion, a two base pair substitution for a single base pair, and a twenty base pair deletion; and wherein expression of functional CMAH in said pig is decreased as compared to a wild-type pig.

16. The method of claim 10, wherein the disruption of said CMAH gene is selected from the group consisting of a four base pair insertion, a two base pair deletion, a single base pair deletion, a single base pair insertion, an eight base pair deletion, a five base pair deletion, a three base pair deletion, a two base pair substitution for a single base pair, and a twenty base pair deletion; and wherein expression of functional CMAH in said pig is decreased as compared to a wild-type pig.

17. A method of producing a glycoprotein of interest, said method comprising a step of incubating an isolated cell capable of expressing said glycoprotein of interest with a cell culture reagent derived from a pig comprising α(1,3)-galactosyltransferase (αGal) and cytidine monophosphate-N-acetylneuraminic acid hydroxylase (CMAH) genes disrupted via gene editing, wherein the amount of N-glycolylneuraminic acid (Neu5Gc) and/or αGal epitopes on said glycoprotein of interest is lower than the amount of Neu5Gc and/or αGal epitopes on said glycoprotein of interest when said isolated cell capable of expressing said glycoprotein of interest is incubated with a cell culture reagent derived from a wild-type pig.

18. The method of claim 17 wherein said glycoprotein of interest is selected from the group consisting of an antibody, a growth factor, a cytokine, a hormone and a clotting factor.

19. The method of claim 17, wherein the disruption of said αGal gene is selected from the group consisting of a 3 base pair deletion adjacent to a G to A substitution, a single base pair deletion, a single base pair insertion, a six base pair deletion, a two base pair insertion, a ten base pair deletion, a seven base pair deletion, and an eight base pair substitution for a five base pair sequence; and wherein expression of functional αGal in said pig is decreased as compared to a wild-type pig.

20. The method of claim 19, wherein the disruption of said CMAH gene is selected from the group consisting of a four base pair insertion, a two base pair deletion, a single base pair deletion, a single base pair insertion, an eight base pair deletion, a five base pair deletion, a three base pair deletion, a two base pair substitution for a single base pair, and a twenty base pair deletion; and wherein expression of functional CMAH in said pig is decreased as compared to a wild-type pig.

21. The method of claim 17, wherein the disruption of said CMAH gene is selected from the group consisting of a four base pair insertion, a two base pair deletion, a single base pair insertion, a single base pair deletion , an eight base pair deletion, a five base pair deletion, a three base pair deletion, a two base pair substitution for a single base pair, and a twenty base pair deletion; and wherein expression of functional CMAH in said pig is decreased as compared to a wild-type pig.

* * * * *

UNITED STATES PATENT AND TRADEMARK OFFICE
CERTIFICATE OF CORRECTION

PATENT NO. : 11,666,039 B2  
APPLICATION NO. : 16/855905  
DATED : June 6, 2023  
INVENTOR(S) : A. Joseph Tector Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 353 days.

Signed and Sealed this  
First Day of July, 2025

Coke Morgan Stewart  
*Acting Director of the United States Patent and Trademark Office*